(12) United States Patent
Steele

(10) Patent No.: US 12,077,736 B2
(45) Date of Patent: Sep. 3, 2024

(54) SYSTEM OF BIOMIMETIC ENERGY SYNTHESIS

(71) Applicant: Dennis Steele, Beaverton, OR (US)

(72) Inventor: Dennis Steele, Beaverton, OR (US)

( * ) Notice: Subject to any disclaimer, the term of this patent is extended or adjusted under 35 U.S.C. 154(b) by 0 days.

(21) Appl. No.: 14/684,401

(22) Filed: Apr. 12, 2015

(65) Prior Publication Data

US 2016/0298066 A1 Oct. 13, 2016

(51) Int. Cl.
| | | |
|---|---|---|
| C12M 1/00 | (2006.01) | |
| C12M 1/02 | (2006.01) | |
| C12M 1/26 | (2006.01) | |

(52) U.S. Cl.
CPC ............ *C12M 21/02* (2013.01); *C12M 23/58* (2013.01); *C12M 31/02* (2013.01); *C12M 33/00* (2013.01); *C12M 41/18* (2013.01); *C12M 43/08* (2013.01); *Y02P 20/59* (2015.11)

(58) Field of Classification Search
CPC ...... C12M 21/02; C12M 21/12; C12M 23/06; C12M 23/58; C12M 31/02; C12M 43/08; C12M 33/00; C12M 41/01
USPC ...................................................... 435/292.1
See application file for complete search history.

(56) References Cited

U.S. PATENT DOCUMENTS

| | | | |
|---|---|---|---|
| 4,341,038 A | 7/1982 | Bloch et al. | |
| 4,554,390 A | 11/1985 | Curtain et al. | |
| 4,952,511 A | 8/1990 | Radmer | |
| 4,958,460 A | 9/1990 | Nielson et al. | |
| 5,565,855 A | 10/1996 | Knibbe | |
| 5,988,761 A | 9/1999 | Yogev | |
| 6,818,026 B2 | 11/2004 | Tateno et al. | |
| 6,993,417 B2 | 1/2006 | Osann, Jr. | |
| 7,222,111 B1 | 5/2007 | Budike, Jr. | |
| 7,452,515 B1 | 11/2008 | Lafleur et al. | |
| 7,563,915 B2 | 7/2009 | Matson et al. | |
| 7,763,457 B2 | 7/2010 | Dunlop | |
| 7,868,195 B2 | 1/2011 | Fleischer et al. | |
| 7,869,904 B2 | 1/2011 | Cannon et al. | |
| 2007/0048848 A1 | 3/2007 | Sears | |
| 2010/0028977 A1 | 2/2010 | Ng et al. | |
| 2010/0207540 A1 | 8/2010 | Walton | |

(Continued)

FOREIGN PATENT DOCUMENTS

KR 20090055170 A * 6/2009 ............ C12M 21/02

OTHER PUBLICATIONS

Kim Z Hun, "English language translation of KR 2009-0055170A", translated on May 1, 2016.*

*Primary Examiner* — Liban M Hassan

(57) ABSTRACT

An improved system of generating renewable energy is comprised of a specific configuration of mechanisms, materials, and processes that all function together as a single symbiotic system. In accordance with a preferred embodiment, the system cultivates aquatic biomass, then extracts triglycerides from said biomass. The extracted triglycerides are converted into biodiesel through transesterification. During the operation of the system, a continuous output of biofuel, thermal energy, steam, and electricity, is efficiently produced. These yields are precisely measured and repurposed as energy input at various points throughout system processes, thus resulting in a surplus output. Any embodiment of the disclosed system will generate a continuously renewable final product of biofuel and power.

13 Claims, 12 Drawing Sheets

(56) References Cited

U.S. PATENT DOCUMENTS

| | | | | |
|---|---|---|---|---|
| 2010/0267104 A1* | 10/2010 | Green | ................... | C12M 21/02 |
| | | | | 435/173.1 |
| 2011/0107664 A1* | 5/2011 | Rancis | ................... | A01G 33/00 |
| | | | | 47/1.4 |
| 2014/0011245 A1* | 1/2014 | Flynn | ....................... | C12P 7/62 |
| | | | | 435/134 |

* cited by examiner

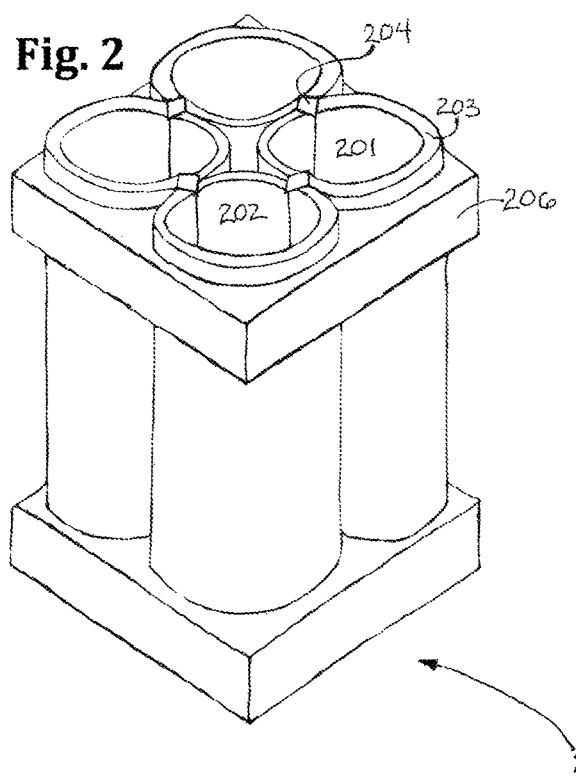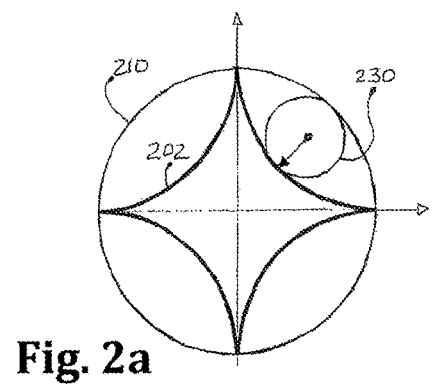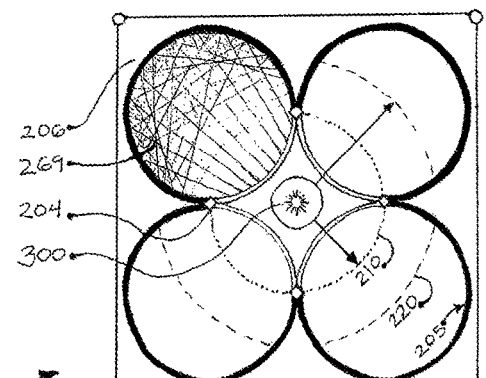
Fig. 2
Fig. 2a
Fig. 2b

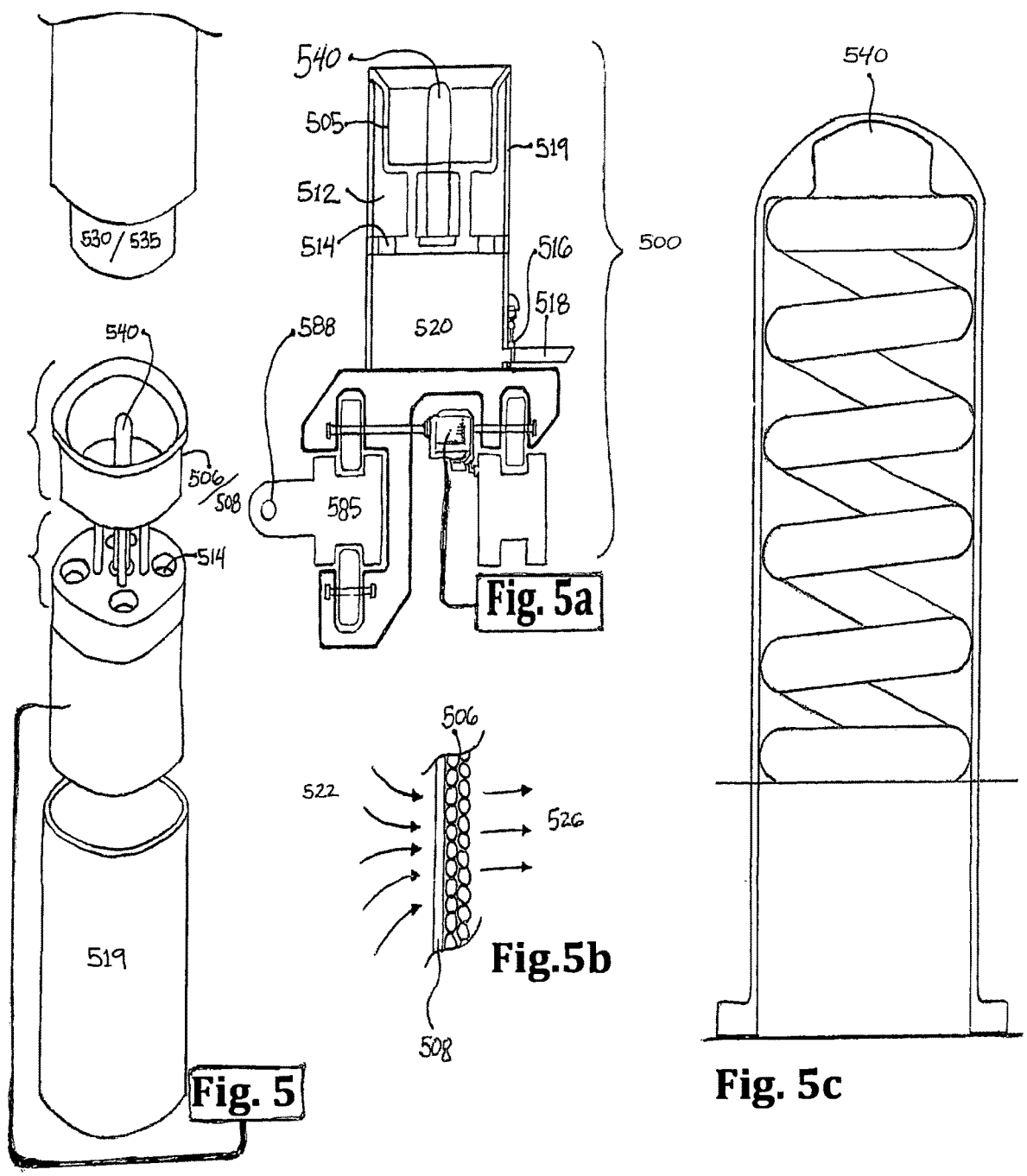

SYSTEM OF BIOMIMETIC ENERGY SYNTHESIS

FIELD OF THE INVENTION

The present invention generally relates to renewable energy, and, more particularly, to an improved system for generating electricity and fuel for industrial consumption. This invention is useful to any organization or community that plans to sustainably produce a continuous output of renewable energy in the form of electricity and biodiesel.

BACKGROUND OF THE INVENTION

Large-scale energy production has been built on an unsustainable infrastructure that largely disregards health risks, environmental costs of carbon emissions, and other destructive aspects of the current industry.

Recognizing this urgent need, a number of cleaner and more efficient renewable technologies are currently being researched, developed, and commercialized, sparking a global energy revolution. New facilities that create renewable energy from wind, solar, biomass, geothermal and other technologies serve as solutions to this basic human need for sustainable energy. In addition to sustainability and efficiency, these renewable energy technologies also create benefits for many people through energy independence.

However, there are currently many disadvantages:

(a) There are high costs in the technical training and support, building of facilities and equipment, and implementation of renewable energy technologies. The large sums of capital invested into the high cost of entry into renewable energy market sectors are often recovered through higher prices for the energy that is produced.

(b) There are great inefficiencies in the various production processes involved in generating reliable power from renewable resources.

(c) Political gridlock, broken market mechanisms and shortsighted planning has made it difficult for industrial energy consumers to get clean, renewable energy at fixed, competitive rates.

(d) A flawed infrastructure, including poorly designed electricity grids, has made the logistics of renewable energy distribution uneconomical.

(e) Biomass is an often-overlooked source of renewable energy. And, even when efficient biomass facilities are put into use, the potential value of byproducts produced by such facilities is not fully realized.

BACKGROUND OF THE INVENTION

Prior Art

Many different types of technologies, concepts, and products that can be named as examples of related prior art stretch across a vast spectrum of differing fields.

Photobioreactor

There have been multiple published descriptions of bioreactors for the cultivation of photosynthetic organisms. For example, U.S. Pat. No. 4,952,511 for a photobioreactor discloses vertical cylinders and an enclosed internally lit cultivation chamber. These design factors do not take into consideration a unique shape that is necessary for simplified and efficient operation of a bioreactor. U.S. Pat. No. 5,958, 761 "Bioreactor And System For Improved Productivity Of Photosynthetic Algae" does include apparatus for the exchange of heat from the within the bioreactor, but it does not provide an efficient reuse of that heat elsewhere in a system. More recent systems and methods disclosed in U.S. Pat. No. 7,763,457 as well as in U.S. Patent Application, Publication Number: US 2010/0028977 A1, also include apparatus for the production of algae. Other publications that have described algae cultivation such as NREL/TP-580-24190 A Look Back at the U.S. Department of Energy's Aquatic Species Program: Biodiesel from Algae. July 1998. However, these examples of prior art do not tackle the problem of the many inefficiencies involved in using algae as a source biofuel and electricity.

Lighting Apparatus

One example, seen in U.S. Patent Application Publication Number US 2010/0207540 A1, discloses a spirally configured HID lamp with specially designed reflective surfaces. This approach does not solve any of the renewable energy industry's problems involved with inefficient wastes of process energy. What is needed is a new type of lighting apparatus, which not only uses the intense radiation of light to illuminate biological photosynthetic processes, but also utilizes the intense radiation of thermal energy elsewhere in the biofuel conversion process.

Algae Oil Extraction and Biodiesel Feedstock

Multiple means and methods for algal separation from an aquaculture medium have been disclosed in U.S. Pat. No. 4,341,038 "Oil Products from Algae," U.S. Pat. No. 4,554, 390 "Method For Harvesting Algae," U.S. Pat. No. 4,958, 460 "Method Of Growing And Harvesting Microorganisms," These examples of prior art describe means and methods of harvesting algae and extracting lipid content from the algal biomass, from individually cultivated batches. Harvesting and extracting single batches do not allow for efficient integration with systems that incorporate continuous processing. U.S. Pat. No. 7,868,195 B2 "Systems And Methods For Extracting Lipids From And Dehydrating Wet Algal Biomass" disclose a specific use of a combination of solvents, centrifugal forces, and membrane filters to ultimately create an ideal biodiesel feedstock from algae. However, this does not include a specific mechanism for integrating any of these methods into a specialized continuous process. An exemplary disclosure in U.S. Patent Application Publication Number US 2007/0048848 A1 "Method, Apparatus And System For Biodiesel Production From Algae" concerns technology that does incorporate these various aspects into a single system. However, an improved system includes its own light source, heat source, and electrical power plant as part of that single system. Not only are additional means and mechanisms necessary, but also an improved design of these new and existing means and mechanisms needs to be combined with a simplified set of steps to accomplish a more efficient process of energy production.

Transesterification

Standard transesterification processes involve a reaction between a triglyceride and an alcohol. Anyone skilled in the art will realize that technologies and methods for industrial transesterification are widely available. For example, U.S. Pat. No. 6,818,026 B2 "Process For Producing Fatty Acid Esters And Fuels Comprising Fatty Acid Ester" utilize feedstock heated to a supercritical state at a temperature above 260 degrees Celsius to facilitate an efficient transesterification reaction. U.S. Pat. No. 7,452,515 B1 "System For Creating A Biofuel" is an example of creating fast reaction rates and continuous processing. U.S. Pat. No. 7,563,915,B2 "Green Biodiesel" uses a solid metallic oxide base catalyst for the transesterification process. Any of these processes are suitable, and it has been proven that many possible ways to successfully conduct transesterification do currently exist. However, these examples of prior art referenced herein do not combine the transesterification reaction as one step within a combination of multiple elements that comprise a single system that functions symbiotically, therefore failing to solve the problem of wasted process energy.

Energy Management Systems

U.S. Pat. No. 5,565,855 "Building Management System" describes technology for transmitting and receiving signals representing energy consumption. U.S. Pat. No. 6,993,417 B2 "System For Energy Sensing Analysis And Feedback" discloses an energy monitoring system. U.S. Pat. No. 7,222,111 B1 "Multi-Utility Energy Control And Facility Automation System With Dashboard Having A Plurality Of Interface Gateways" discloses a system for comparing and analyzing energy consumption and production patterns. U.S. Pat. No. 7,869,904 B2 "Utility Load Control Management Communications Protocol" describes various means for controlling electrical loads. Although these examples of prior art disclose technology that is useful in each of their respective applications, none of them truly adhere to the concept of industrial metabolism, consequently rendering them unable to completely solve inefficiencies specific to renewable energy production. What is needed is a combination of all of the means and mechanisms and methods involved in building and facility management, industrial process automation, and the analysis of energy usage patterns, and all of it must be specifically designed as a single integrated system. Such an integrated system should simplify all of the many complexities of renewable energy production into one symbiotic process, therefore solving existing problems with energy efficiency.

SUMMARY

In accordance with the present invention, there is provided an improved method of creating commercial energy products from a biological source using a specific configuration of mechanisms, materials and processes that function together as a symbiotic system. This system utilizes organic matter within living species of algae and results in highly efficient production of a continuous output of renewable biofuel and electric current.

The present invention improves upon the current design, construction and operation of photobioreactors, lighting apparatus, algae oil extraction systems, biodiesel processors, and energy management systems. Notwithstanding these examples of prior art and any other technologies in current use, the present invention is neither taught nor rendered obvious thereby. The present invention is unique in that it combines each of its basic elements: a Hypoclycloidal Bioreactor, a Photothermal Generator, a Clockwork Extraction Cycle, a Biodiesel Tank Farm, all according to biomimetic concepts applied to renewable energy, thus integrating the system in such a way that all of its basic elements function as a whole. In order to achieve this type of integration, the present invention simplifies all of the many industrial complexities of renewable energy production into three stages of operation: the cultivation stage, extraction stage and conversion stage. An SBES Manager regulates and automates all energy input and output, or the industrial metabolism, of these three different stages enabling them to operate as one symbiotic process, therefore solving problems with efficiency.

DRAWINGS

A complete understanding of the present invention may be obtained by reference to the accompanying drawings, when considered in conjunction with the subsequent detailed description, in which.

Figure 2C:
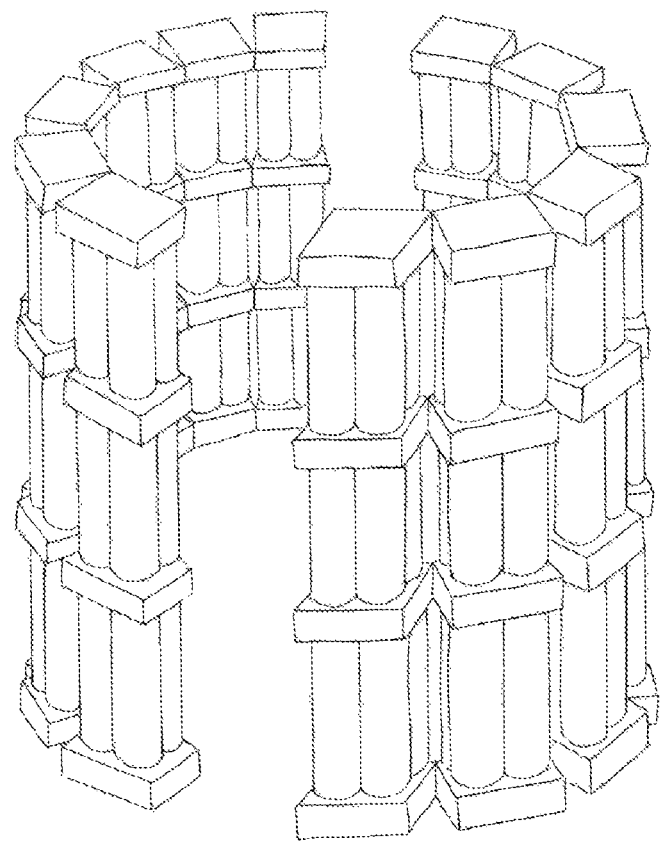
FIG. 2, 2a, 2b, 2d show aspects of the Hypocycloidal Bioreactor Module
Figure 4:
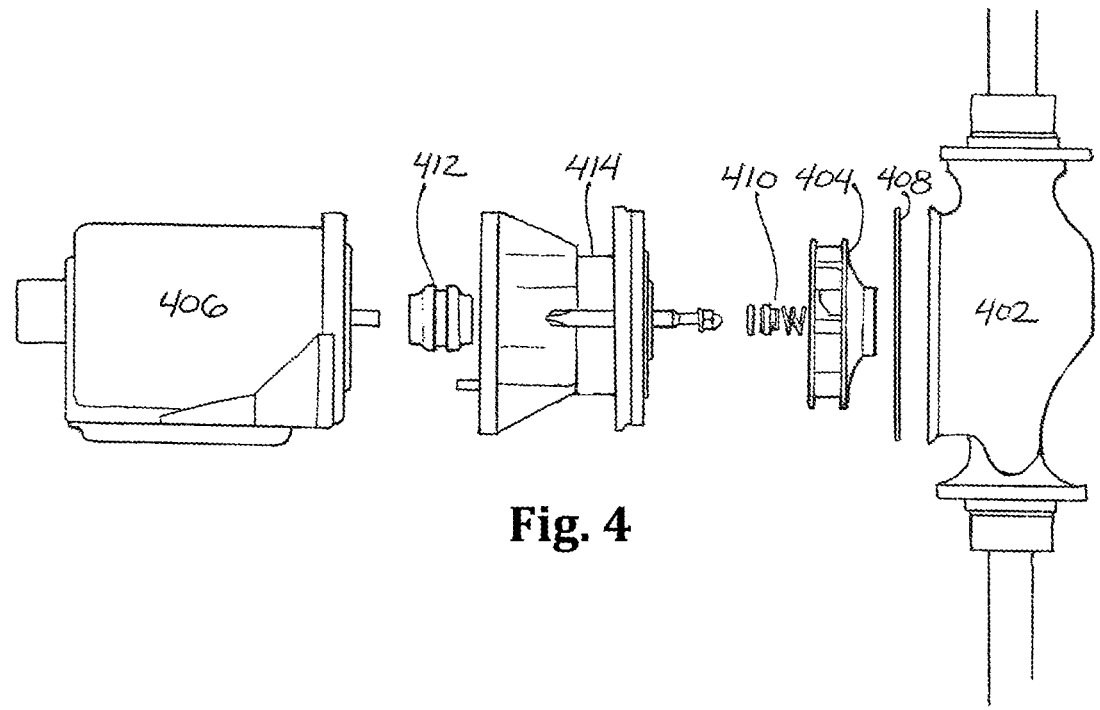
Figure 4A:
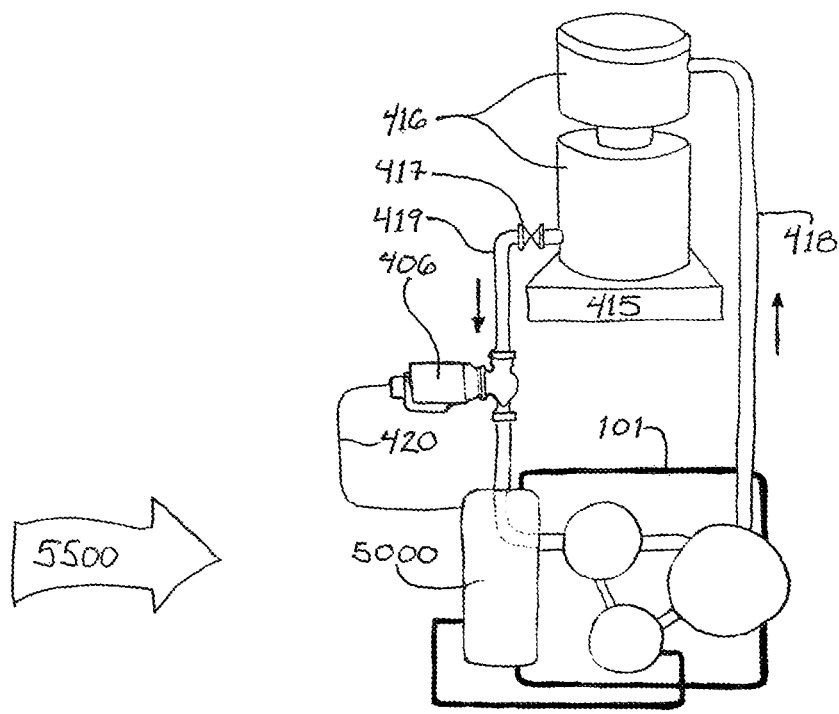
Figures 5D, 5E:
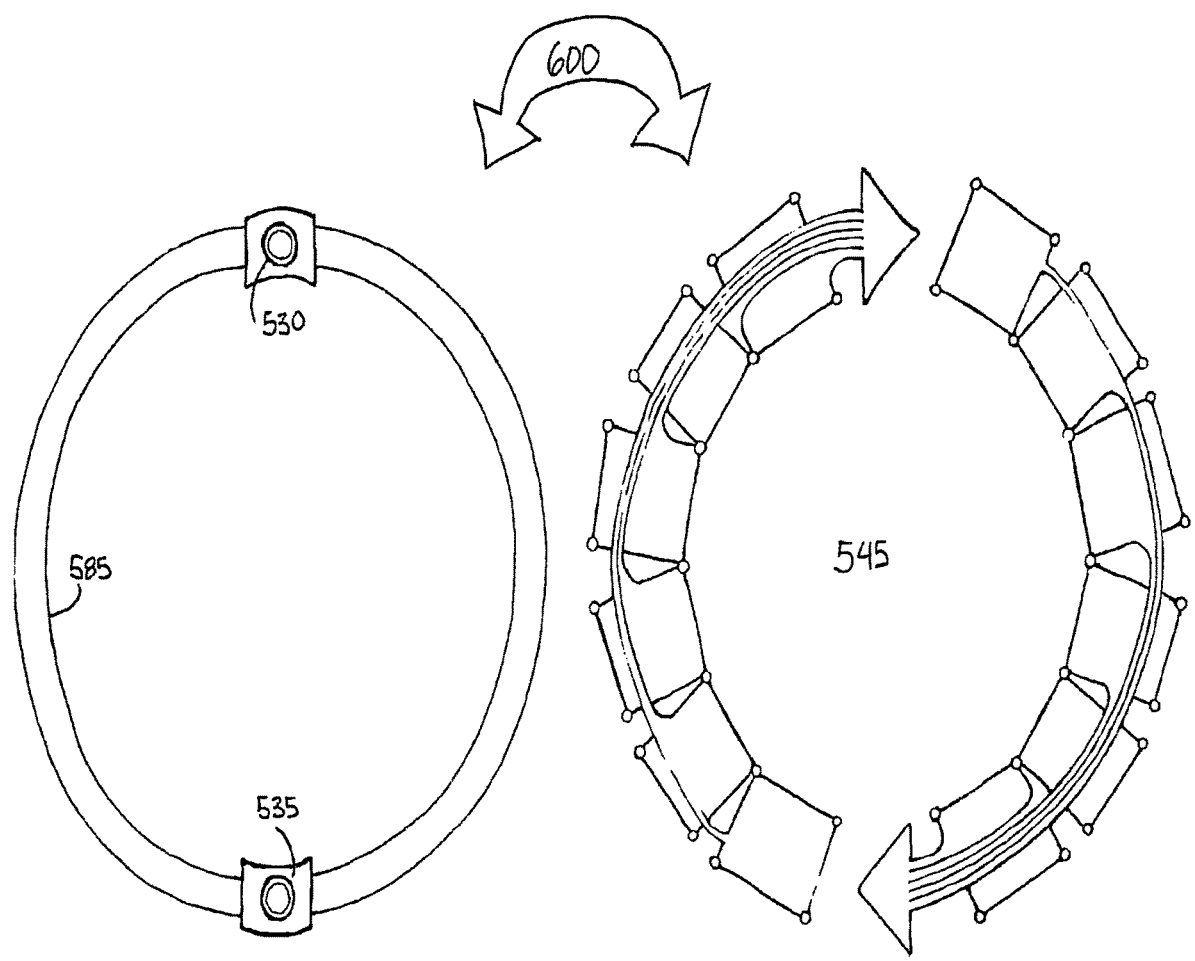
Figure 6:
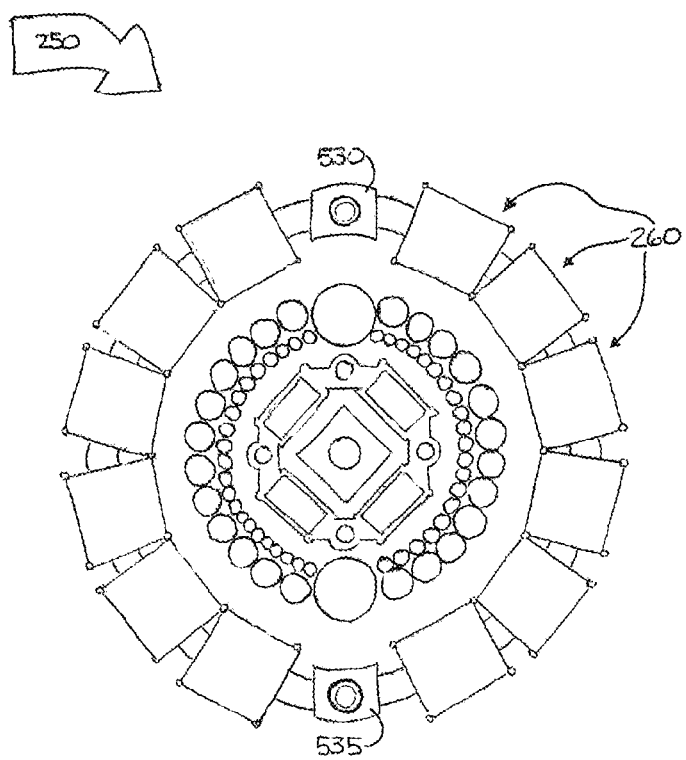
Figure 6A:
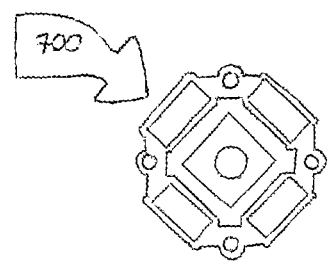
Figure 6B:
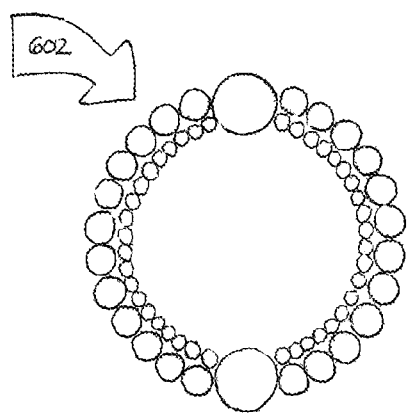
Figure 7:
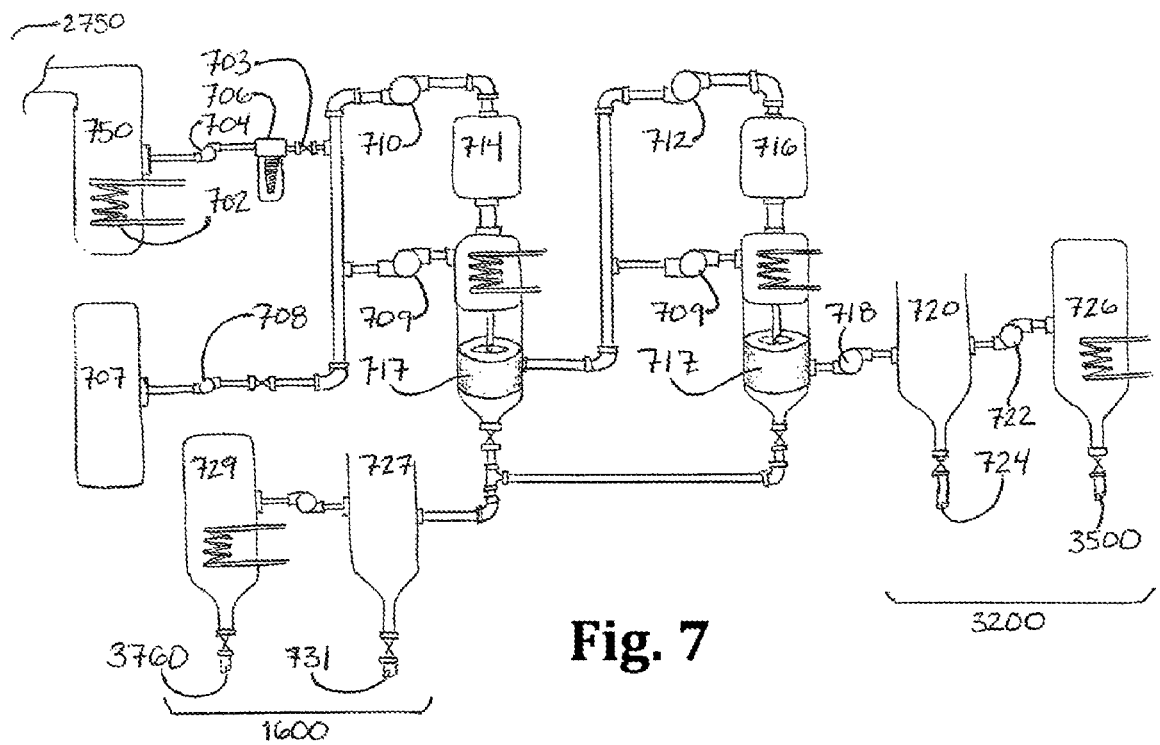
Figure 8:
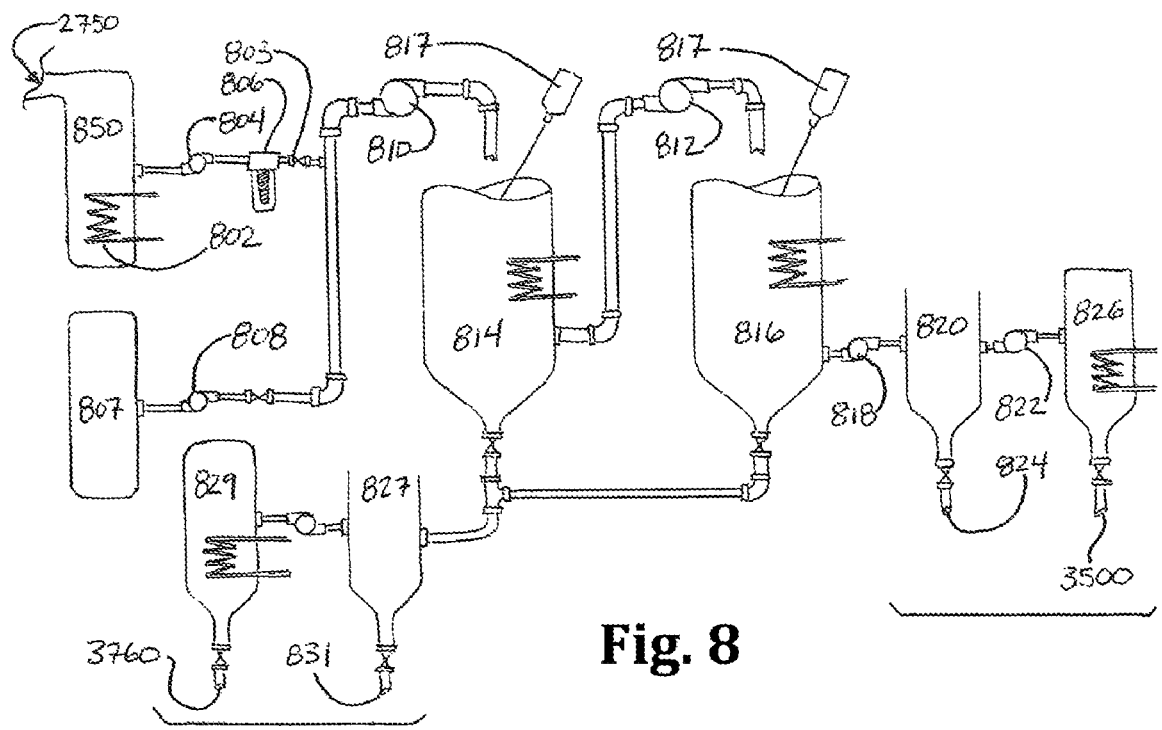
Figure 9:
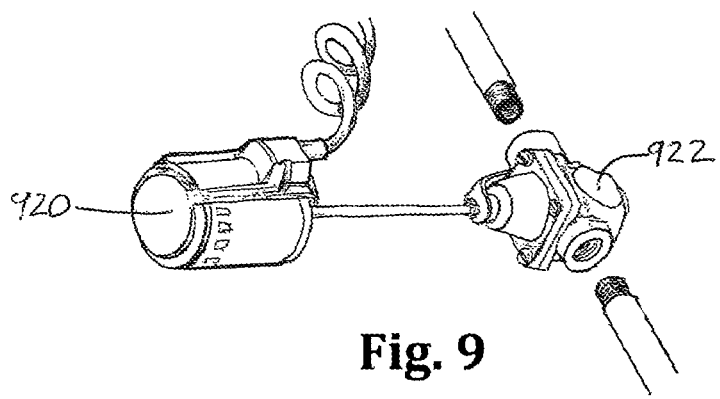
Figure 9A:
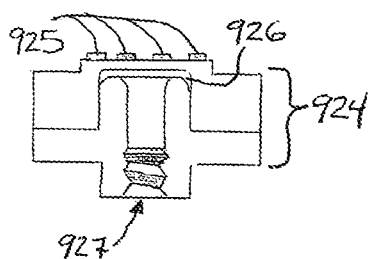
Figure 9C:
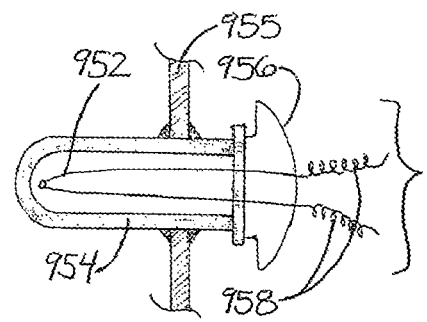
Figure 9B:
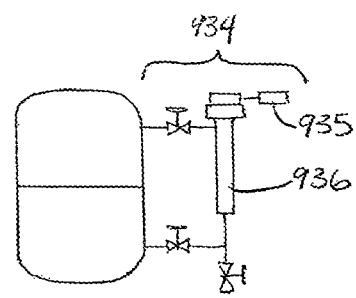
Figure 9D:
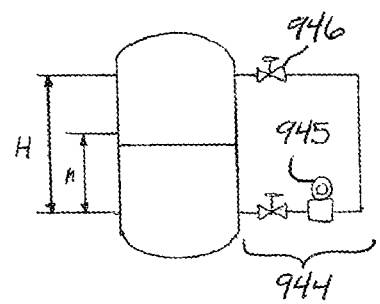

FIG. 2c is a shows multiple Hypocyloidal Bioreactor Modules configured into a Hypocycloidal Bioreactor Array FIG. 3, 3a, 3b, 3c, 3d, 3e is a graphically describe various aspects of the Photothermal Generator FIGS. 4 and 4a show the Hydrocycle Subsystem FIG. 5, 5a, 5b, 5c, 5d, 5e are explanatory diagrams of the Clockwork Extraction Cycle FIG. 6, 6a, 6b show plan views of one embodiment of a Biodiesel Reaction Complex FIGS. 7 and 8 illustrate aspects of the transesterification process FIG. 9, 9a, 9b, 9c, 9d show various instrumentation and control mechanisms used by the SBES Manager (For purposes of clarity and brevity, like elements and components will bear the same designations and numbering throughout the Figures.)

DRAWINGS

Reference Numerals

1000 cultivation stage
1500 algal biomass output
2000 extraction stage
2250 SVO output to PEB Genset
2750 triglyceride feedstock
3000 conversion stage
3500 biodiesel output
3750 electrical current output
3760 semi-refined glycerol
3770 agrichar
3780 cellulosic feedstock
3790 other by-products
3999 water
4000 steam
5000 SBES Manager
5500 Hydrocycle subsystem
5750 small-scale hydroelectric generator
6000 PEB genset
6100 carbon dioxide processor
200 Hypocycloidal Bioreactor Module
201 cultivation chamber
300 Photothermal Generator
202 hypocycloid lens
203 chamber wall
204 mullion
205 optical substratum
206 structural joint
210 MRA (minimum radiation area)
220 ARA (average radiation area)
230 PTG (outer circumference of Photothermal Generator)
250 SBES bireactor array
260 module stacks
269 reflected light
302 evaporator housing
304 condensing reservoir
306 compressor
308 expansion valve 310 high-pressure refrigerant (condensed gas)
312 low-pressure refrigerant (vaporized gas)
313 thermally conducive material
314 sealed-air insulating barrier
316 reflective surface
318 high-intensity discharge spiral
321 light
322 heat
323 water
324 steam
320 steam output valve
101 schematic overview of SBES
5500 Hydrocycle subsystem
402 gravity interface volute
404 hydrocycle impeller
406 small-scale hydroelectric generator
408 gasket
410 seal
412 coupler
414 shaft assembly
415 crown module
416 cooling tanks
417 automated hydrocycle valve
418 rising steam
419 falling water
420 hydroelectric output
500 harvester apparatus
505 biomass receptacle
506 restraint screen
508 aquatic divider membrane
510 extraction drain assembly
512 drain compartment
514 drain aperture
516 drain valve
518 drain output
519 extraction canister
520 aquaculture process tank
522 aqueous medium
524 algal biomass
526 semi-refined triglycerides
530 frontside hydraulic press
535 backside hydraulic press
540 resistive spring mechanism
542 clockwork timetable
545 drainpoints
585 extraction track
586 motor
588 hinge
250 SBES Bioreactor Array
260 module stacks
600 Clockwork Extraction Cycle
602 SBES tank farm
700 biodiesel reactors and associated apparatus
1600 glycerol phase
2750 triglycerol feedstock
3200 biodiesel phase
3500 refined biodiesel
750 algal oil triglycerides tank
702 stem-powered heat coil
703 automated valve
704 triglyceride injection pump
706 filter
707 alcohol and catalyst tank
708 alcohol and catalyst injection pump
709 alcohol and catalyst re-injection pump
710 CSTR main input pump 1
712 CSTR main input pump 2
714 CSTR 1
716 CSTR 2
717 centrifuge
718 ester pump
720 wash and neutralizer tank
722 washed ester pump
724 wash water and salts
726 drywash tank
727 glycerol neutralizer tank
729 glycerol dryer tank
3760 semi-refined glycerol
731 salts
850 algal oil triglycerides tank
802 steam-powered heat coil
803 automated valve
804 triglyceride injection pump
806 filter
807 alcohol and catalyst tank
808 alcohol and catalyst injection pump
809 alcohol and catalyst re-injection pump
810 batch tank input pump 1
812 batch tank input pump 2
814 batch tank 1
816 batch tank 2
817 mixer
818 ester pump
820 wash and neutralizer tank
822 washed ester pump
824 wash ester and salts
826 drywash tank
827 glycerol neutralizer
829 glycerol dryer tank
3760 semi-refined glycerol
831 salts
920 pnuematic motor
922 automated valve
924 pressure transducer
925 elements
926 diaphragm
927 pressure
934 displacer meter
935 displacer transmitter
936 displacer chamber
944 differential pressure meter
945 differential pressure transmitter
946 pressure taps
950 thermocouple device
952 thermocouple junction
954 thermowell
955 vessel wall
956 external cap
958 wires

DETAILED DESCRIPTION OF THE PREFERRED EMBODIMENT

Since other modifications and changes in order to fit a variety of particular operating requirements and environments will be apparent to those skilled in the art, the invention is not considered limited to the example chosen for purposes of disclosure, and covers all changes and modifications which do not constitute departures from the true spirit and scope of this invention.

It is a fact that most of the original organic matter that has become today's geologic formations of petroliferous deposits, was once algae. Immense quantities of algae in shallow prehistoric bodies of water were buried by sediments and subsequently transformed by pressure and heat over millions of years into petroleum.

Today, this process can be shortened to within a couple of days, or even less, with proper utilization of the System of Biomimetic Energy Synthesis (SBES). At present, I believe that the following describes an embodiment that operates the most efficiently, but other embodiments are also satisfactory.

Dimensions, materials, and values of certain components are specified in gross detail because the SBES is designed to function efficiently at both large and small scales; certain aspects of this description must remain generalized yet accurate enough to allow for both small-scale and large-scale systems. The following parts of this specification have been written with consideration of scalability issues, while also taking into consideration accuracy completeness. Any person skilled in the art and currently working in the field of biofuel production will have sufficient knowledge of basic details that such a person should easily be able to build and use a functioning SBES within a new or existing facility from the information that is contained in this specification.

In the interest of fully meeting all requirements of patent specifications and creating a clear, concise and complete description of how to make and use the SBES, the following specification shall be divided into three distinct detailed descriptions:

Conceptual Section

Shall fully describe the biomimetic precepts imposing a standard of design based on biological models. The concept of a design that mimics nature is the underlying principle used in designing the SBES.

Construction Section

Shall be a description of mechanisms, materials, and equipment necessary to build the SBES.

Operation Section

Shall be a description of all operational aspects involved in the successful use of the SBES.

DETAILED DESCRIPTION

Conceptual Section

This specification shall begin with a description of the concepts involved and the theories that are used as a premise for the technology. This conceptual description includes testing central assumptions about energy production and industrial engineering by creating a renewable energy system that has been inspired by nature. According to conventional engineering and business methods, new technologies are considered risky and are often deemed as not cost-effective.

However, the truth is: the costs we incur, as a society of interlinked communities of human beings, to implement new ideas into scholarly thought, political structures, and industrial mechanisms, is vastly higher than the costs nature incurs to design ideas into and out of ecosystems. So, by using biological design processes as a model, m more natural, efficient, and cost-effective integration of new technologies can be discovered.

The concept of biomimetic development, at its most fundamental level, is modeling technology and methods after natural examples of biology found in the environment. The SBES aims to use this concept to motivate and coordinate collaborative effort among diverse academic, political, and industrial disciplines in a common direction toward a cleaner, more efficient, more prosperous energy industry. The result is a wiser, more natural conversion of energy.

Once people come to fully understand the inherent benefits of the SBES they will be eager to give up on the stagnant technology, bloated cost-structure, and unsustainable characteristics of the current industry. Once the public values and perceptions include the reality of the SBES, communities will be eager to leave behind the archaic forms of energy, and embrace the benefits of a new technology. Once we are able to elevate our awareness and release ourselves from the stranglehold of an obsolete industry, we can then begin to truly show the world direct links between healthy ecosystems and economic prosperity.

Ultimately, this kind of public momentum can allow a consensus to emerge among the diametrically opposed economists and ecologists . . . because the driving force behind this technology is not environmentalism. The real driving force is efficiency!

DETAILED DESCRIPTION

Construction Section

To begin a description outlining the construction of an SBES it is necessary to outline its major parts:
SBES Manager
Hypocycloidal Bioreactor Module
Photothermal Generator
Clockwork Extraction Cycle
Biodiesel Reaction Complex As the following description goes further into detail for each of these major parts, drawing figures and reference numerals are indicated in parenthesis where applicable.
SBES Manager The SBES Manager enables analysis, regulation, and automation of an SBES facility. The SBES Manager is comprised of instrumentation, controls, and computer processing that enables the intelligent use of raw materials and process energy in such a way that the end result is a seamless integration of various system elements and a highly-efficient final output of renewable energy.

Construction of the instrumentation and control mechanisms of an SBES manager shall include means and mechanisms necessary to monitor and regulate components of the Cultivation Stage 1000, the Extraction Stage 2000, and the Conversion Stage 3000. Throughout these three stages, the SBES Manager shall identify and analyze energy consumption and production patterns. The manner in which the SBES Manager processes information regarding such patterns shall be known as SBES industrial metabolism. Construction of the instrumentation and control mechanisms of an SBES manager shall include all other systems hardware necessary throughout the entire SBES in order to efficiently regulate the SBES industrial metabolism.

Constructing an SBES facility involves interconnected sets of systems that the SBES Manager coordinates to work together. The SBES Manager regulates all subsystems hardware. The primary components include: Hydrocycle Subsystem 5500, PEB Genset 6000, Carbon Dioxide Processor 6100, and Control Loop.

According to the preferred embodiment, one example in which these biomimetic concepts shall be applied to the SBES process is through the use of a Hydrocycle Subsystem. The Hydrocycle Subsystem is a complete subsystem within the SBES, utilizing water as a means of extracting heat from aspects of the Cultivation Stage, to generate steam for use in the Conversion Stage. In the process of putting the temperatures and pressures of the steam to work in various aspects of the SBES process, the steam is raised to Hydrocycle Tanks located at the top of the structure, where ii is allowed to cool into water. As the Hydrocycle Tanks become filled, automated release valves allow the liquid contents to fall through turbines that draw current from the natural force of the falling water. The resulting current is fed into the SBES Energy Manager, and the water continues back into the cultivation stage to complete the cycle. In describing the construction of the Hydrocycle Subsystem, references to FIG. 4 and FIG. 4a are made in order to fully describe individual parts in detail and the ideal construction of a first embodiment.

Rising steam 418 that has condensed into water is stored in the cooling tanks 416. An automated hydrocycle valve 417 linked to a control loop within the SBES Manager releases falling water 419. The falling water 419 reaches a gravity interface volute 402. A standards gasket 408 used to create a watertight housing for the hydrocycle impeller 404 within the gravity interface volute 402.

The force of the falling water 419 rotates the hydrocycle impeller 404. The rotational force of the hydrocycle impeller 404 is transferred to the shaft assembly 414. The shaft assembly 414 is connected to the electrical generating shaft of small-scale hydroelectric generator 406. Through this mechanism, the same rising steam 418 that is put to use elsewhere in the SBES process eventually becomes falling water 419 used to generate hydroelectric output 420.

At the top of each individual module stack 260, a crown module 415 is mounted. There can be numerous crown modules as part of a larger assembly of numerous hydrocycle subsystems that ultimately drive the output of numerous small-scale hydroelectric generators 406.

The hydrocycle rate is the specific rate that rising steam accumulates into water in cooling tanks located in each crown module 415, in combination with the total process demands for hydroelectric output 420. The hydrocycle rate shall be monitored and regulated by the SBES Manager.

PEB Genset

During the extraction stage, triglyceride content is completely separated from the harvester algae. The algal biomass yields high-quality organic-based oil. The SBES Manager divides the resulting yield into two output streams. One output becomes input to the conversion stage, when the plant oil is processed into a marketable commercial product: ASTM D 6751 biodiesel. The other stream shall be directed to specialized diesel engines that have been modified to run on straight vegetable oil, or SVO.

The diesel engines power electric generators that provide a greater amount of power than the entire SBES facility can consume, therefore generating a substantial power surplus. This power surplus becomes one of the primary commercial products produced by the SBES facility.

The diesel engines could easily be operated using the refined finished product, ASTM D 6751 biodiesel, resulting from the SBES conversion stage. However, this creates higher operating costs because of the additional process energy necessary to convert plant oil into biodiesel.

In order for the SBES Manager to effectively regulate this vital aspect of the SBES, the diesel engines must be specially designed to accommodate SVO, as well as integration with the SBES industrial metabolism. This specialized design shall be known as a Premium-Efficiency-Biomass Engine and Generator Set, or PEB Genset 6000.

The viscosity of the algae oil compared to biodiesel is the primary reason that the specialized design of the PEB Genset is necessary. Modifications to the fuel, in the form of viscosity transformation must be made in order to bridge the compatibility gap. The PEB Genset shall employ means and methods of applying sufficient heat to reduce the algae oil viscosity to a level compatible for use directly in the compression-ignition component of the PEB Genset. The PEB Genset 6000 shall include a steam-heated tank in which algae oil is maintained at a temperature above 176 degrees Fahrenheit (80 degrees Celsius). The PEB Genset's steam-heated tank will ensure SVO viscosity will be equal to that of standard diesel fuel, allowing the engine to operate.

This process of viscosity transformation is an ideal one, since the SVO can be kept hot using steam energy from the output of the Photothermal Generator. The SBES Manager controls these materials and mechanisms by processing SBES industrial metabolism information, enabling the PEB Genset to produce electrical output as a true energy surplus.

It is simple for additional modifications to engine timing, fuel drainback, fuel lines and other considerations to be made by any diesel technician skilled in the art, in order to optimize engine performance characteristics for the use of vegetable oil in compression-ignition engines. Another way of expressing this is to address the common considerations for the use of SVO in diesel engines.

The PEB Genset 6000 shall be attached to the exhaust gas outlet. This exhaust gas outlet is connected to a Carbon Dioxide Processor 6100. The Carbon Dioxide Processor is where exhaust carbon dioxide and thermal energy are processed for reuse.

Proper use of SVO in a PEB Genset is crucial to the efficient operation of an SBES facility. The advantages using SVO over refined ASTM D 6751 biodiesel are significantly reduced chemical engineering and conversion costs, as well as improved emissions, lower overall energy consumption and substantially increased efficiency.

Output from the extraction stage 2000 feeds SVO output to the PEB Genset 2250, essentially supplying fuel input for the electrical power output. In turn, through the Carbon Dioxide Processor 6100, the SBES Manager 5000 monitors and regulates PEB carbon dioxide output and thus feeds the extracted and processed carbon dioxide to the Hypocycloidal Bioreactor Modules 200, thereby completing an efficient cycle of biomass production.

Thus, there is a vast improvement to the overall energy lifecycles of the materials used in the SBES. The PEB electricity output powers the Photothermal Generator as well as other power consumption demands throughout the SBES process.

Carbon Dioxide Processor

The idea of converting waste streams into resources is gaining more and more acceptance among the current industrial, political and regulatory framework of the United States. This can be seen in various implementations of recycling and material recovery methods and technologies.

Progressive strategies that reduce, reuse and recycle waste are more environmentally and economically attractive than ever. This is especially true in terms of the specific way this progressive strategy has been applied to the construction of the Carbon Dioxide Processor 6100.

A critical aspect of the SBES Manager involves its capacity to regulate the pH balance, the pressure, and the exact content of the PEB Genset exhaust gases. The SBES Manager handles these tasks through the use of the Carbon Dioxide Processor 6100. The Carbon Dioxide Processor 6100 is a subsystem of instrumentation and control within the SBES Manager, and shall include all means and methods necessary to efficiently recapture carbon dioxide and other materials within the exhaust gases from the PEB Genset.

The carbon content produced by the Carbon Dioxide Processor 6100 shall be carefully monitored and controlled by the SBES Manager, and fed to the algal photosynthesis taking place within the cultivation stage.

Control Loop

The construction of the SBES Manager shall include all means and mechanisms necessary for the complete and efficient monitoring, control and automation of SBES industrial metabolism. This shall be accomplished through the implementation of a control loop. Instrumentation shall measure key process variables throughout the SBES process.

The measurements shall be processed in real-time according to specialized SBES Manager hardware and software. The signals from process instrumentation are translated into data by the SBES Manager hardware and software, cross-referenced and correlated with process specifications, and ultimately trigger precision responses from automated control mechanisms.

The control loop shall be constructed in such a way that accurate instrumentation signals are generated from the following process variables:

Luminous Flux (Photothermal Generator)
Heat exchange rates
Algae photosynthesis rates
Carbon Dioxide Processor rates
Process energy consumption rates
Hydrocycle rates Temperature, pressure, level and flow measurements within the Biodiesel Reaction Complex.

Continuous real-time measurements of total energy and material inputs, compared to continuous real time measurement of total energy and material outputs, ensuring the production of a true energy surplus.

These components shall be constructed in a way that allows the mechanisms to be operated by the SBES Manager in a way that ensures a consistent and efficient final output of ASTM D 6751 biodiesel output and electrical output.

Hypocycloidal Bioreactor Modules

A series of tanks will be used to cultivate algae. The carbon dioxide in the exhaust gases emitted from PEB Generators is processed into an input stream with a carefully controlled pressure, temperature and pH balance. This input stream is mixed into an aqueous medium, combined with the light and heat radiated by the Photothermal Generator, enabling Hypocycloidal Bioreactor Modules to cultivate vast amounts of algae very quickly and economically. Using the Photothermal Generators within the Hypocycloidal Bioreactor Arrays, the SBES Cultivation Stage maintains an environment conducive to growing algal biomass until ready for harvest.

Figure 2D:
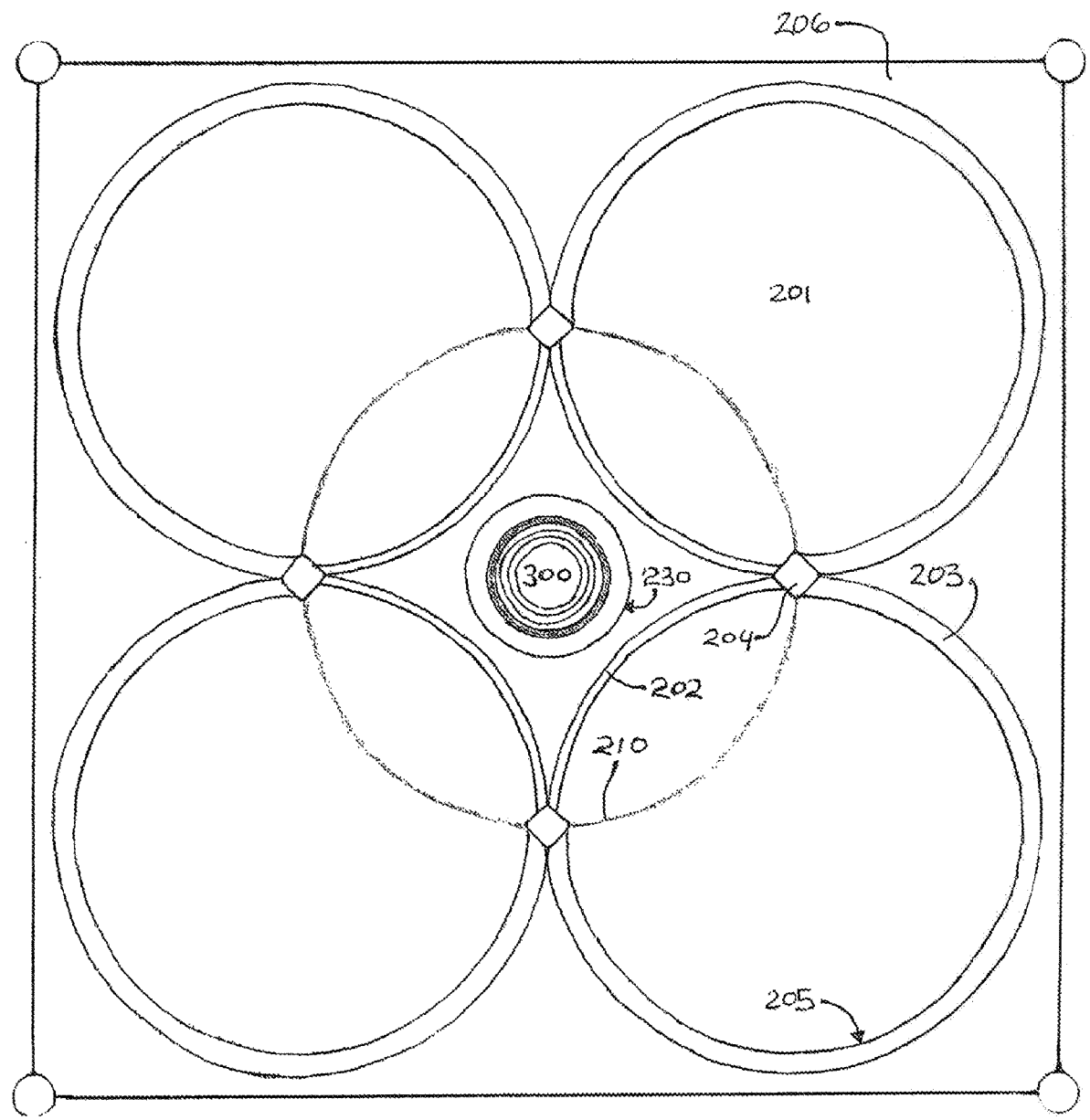
Figure 3:
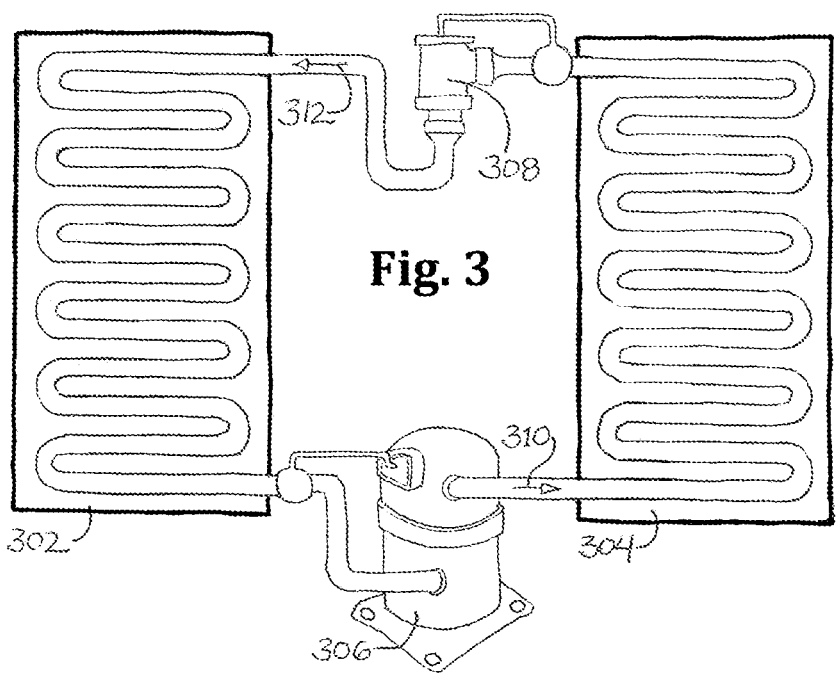
Figure 3A:
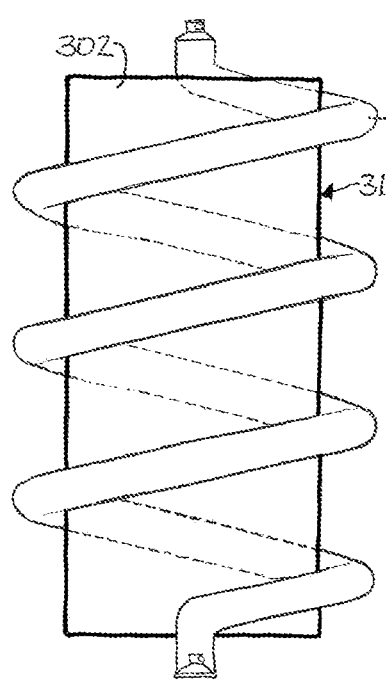
Figure 3B:
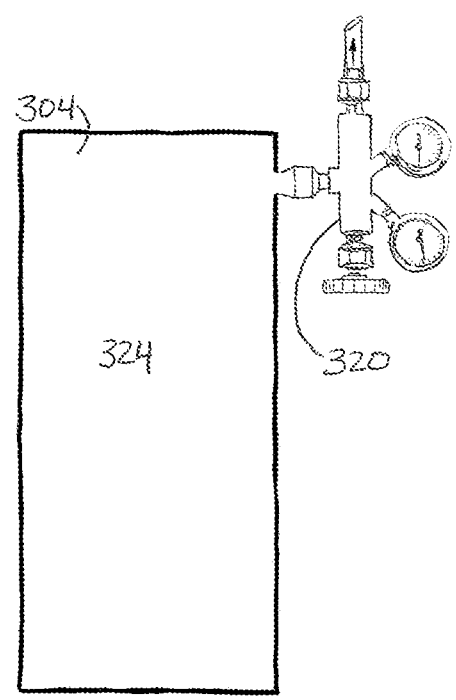
Figure 3C:
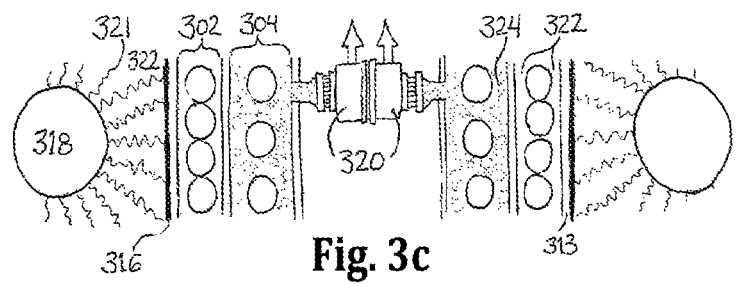
Figure 3D:
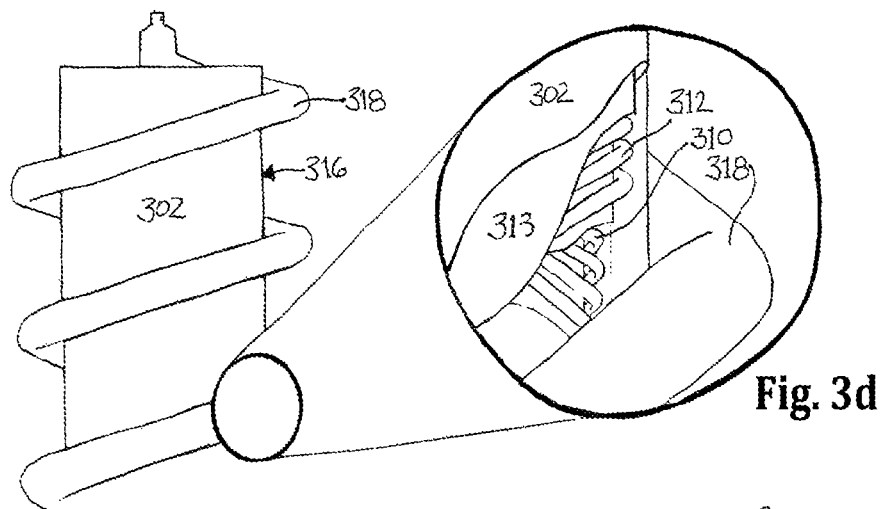
Figure 3E:
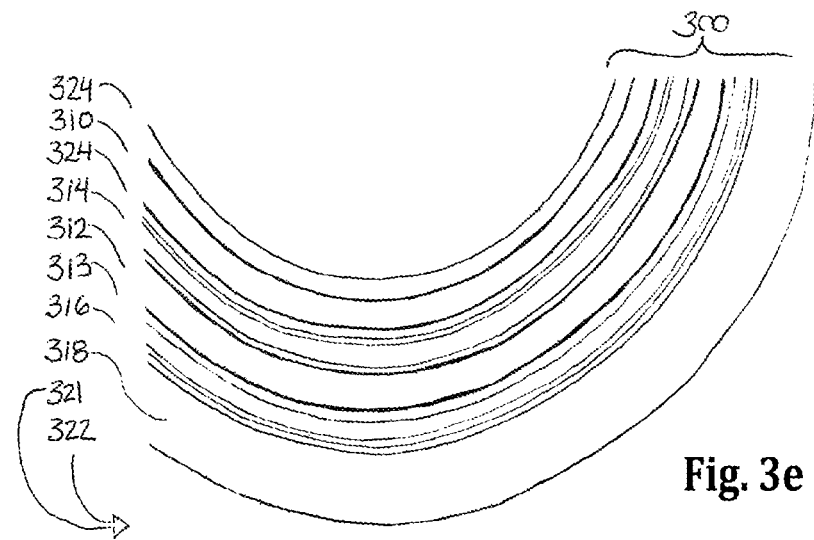

Receiving the carbon dioxide processor output is the Hypocycloidal Bioreactor Module shown in FIG. 2. An SBES Bioreactor Array as shown in FIG. 2*c* is comprised of individually constructed Hypocycloidal Bioreactor Modules. This allows various scalable configurations of SBES facilities to be adapted to a wide range of locations and industrial applications.

In order to build a Hypocycloidal Bioreactor Module, an important set of geometric measurements of physical parameters must be accurately defined. The Hypocycloidal Bioreactors an equipped with Photothermal Generators that produce light and heat. The end result of Hypocycloidal Bioreactor Module operation is a continuous output of algae and steam. Each module has four cylinders with a hypocycloidal space in the center. The following geometric constructs determine the scale and shape of the Hypocycloidal Bioreactor Module. FIG. 2*a* shows the geometric constructs necessary for the construction of this aspect of the SBES.

MRA 210 is the minimum radiation area of the high-intensity light discharged from the Photothermal Generator 300. This is the minimum radiation area, measured in lumens that that will be necessary for successful algae growth and photosynthesis within the SBES Cultivation Stage 1000.

PTG 230 is the outer circumference of the HID lamp of the Photothermal Generator.

ARA 220 is a measurement of luminous flux, or the rate of flow of electromagnetic waves in the visible spectrum, within a Hypocyloidal Bioreactor Module. This measurement is taken at multiple points around the circumference of a given circle, representing an average level of light radiated throughout the entire volume of a Hypocyloidal Bioreactor Module.

There shall be a distinct point chosen on the outer circumference of the Photothermal Generator, and this point shall be used to form a hypocycloid with four cusps. The geometric formula for creating a hypocycloid is well known by anyone skilled in geometry, and the hypocycloid shape has a specialized role in determining the exact shape of the hypocycloidal lens 202.

The hypocycloidal lens 202 is constructed from transparent material, and is positioned at the core of each Hypocyloidal Bioreactor Modules. The shape of a hypocycloidal lens is a precise representation of a geometric formula derived from the above measurements. This geometric expression, which determines the shape of the hypocycloidal lens, is defined by the measured motion of a distinct point, P 240, on the PTG 230, as it completes one revolution inside MRA 210.

The hypocycloidal shape is connected to chamber walls to form four cylindrical tanks. The hypocycloidal shape is constructed of transparent material. There is a structural joint and seal between the transparent hypocycloidal shape and the chamber walls. The interior surface of the cylindrical chamber is covered with a highly reflective surface. These parts are combined to form specialized tank system that shall be known as a Hypocyloidal Bioreactor.

Each Hypocyloidal Bioreactor is designed to interconnect to another by being stacked vertically together, forming a larger cylindrical array. At the top of the stack, a cap module shall be attached. At the base of the stack, is a drain fitted to a harvester apparatus 500. Once the algal biomass within the Hypocyloidal Bioreactors is ready for harvest, its contents are drained and pumped from the cultivation stage and into the extraction stage.

Photothermal Generators

In the vacant space between the four cylinders at the center of the given circle is a photothermal generator 300. The photothermal generator 300 emits a measured area of light radiation 321 and that measurement shall be equal to the given circle. The light is produced by a high-intensity discharge lamp in the shape of a spiral 318, mounted outside of the cylindrical surface of an evaporator housing 302.

The high-intensity discharge spiral 318 produces an intense concentrated output of light 321 by the discharge of electricity between electrodes in a metallic vapor in a sealed glass enclosure. The preferred and most basic embodiment involves the use of high-pressure sodium sealed into the spiral tube to produce a broad spectrum of golden-white light by means of electric discharge in sodium vapor.

The evaporator housing 302 is made of a thermally conducive material 313 with a light-reflective exterior surface 316. Within is tubing suitable for holding a volatile refrigerant capable efficient heat transfer. This evaporator housing forms one element of a system that uses a cycle of operations equivalent to those of a heat pump.

As the volatile liquid, or refrigerant, passes through the evaporator housing 302 it boils into a vapor, extracting heat from the close proximity of the high-intensity discharge spiral 318. A tube that is coiled near the interior surface of the evaporator housing 302, is what holds the volatile substance such as ammonia, sulfur dioxide, or haloalkane, capable of doing this work The coiled tube is connected to an industrial-grade compressor, where its temperature and pressure is raised adiabatically.

Tubing from the compressor 306 is connected to a condensing reservoir 304 that contains a volume of water. It is within this part of the system where the high-pressure refrigerant 310 discharges its heat into water 323, creating steam 324 pressure within the SBES condensing reservoir 304. In this way, heat 322 extracted from the close proximity of the high-intensity discharge spiral 318 is used to generate steam 324 that can be used as energy input for other aspects of the SBES.

The steam 324 in the condensing reservoir 304 is released through a steam output valve 320, and the refrigerant is now in a condensed liquid state 310. The refrigerant then passes an expansion valve 308 through which the high-pressure refrigerant 310 is allowed to expand before entering the evaporator housing 302, where it takes up heat from its surroundings and becomes a vapor again 312, thus completing the cycle.

Clockwork Extraction Cycle

FIG. 5 shows details of a harvester apparatus 500. In the harvester apparatus 500, which is comprised of numerous components within an extraction canister 519. These components shall consist of a biomass receptacle 505 that receives the algal biomass output 1500, the extraction drain assembly 510, and the aquaculture process tank 520.

FIG. 5a shows further details of a harvester apparatus 500 as it is positioned upon the extraction track 585. A motor 586 used as a means of carrying the harvester apparatus to prescribed locations on the extraction track 585 and a hinge 588 shall be used as a means of emptying cellulosic matter and other remains that are left in the biomass receptacle 505 once the triglycerides have been extracted. The biomass receptacle 505 receives all of the algal biomass output 1500. A restraint screen encloses an aquatic divider membrane 508 that separates the components of the algal biomass 524. An extraction canister 519 houses an extraction drain assembly 510 is a space in which the semi-refined triglycerides 526 pass through a drain compartment 512, then falling through a drain aperture 514 into an aquaculture process tank 520. Drain output 518 of the harvester apparatus 500 is managed by an automated drain valve 516.

FIG. 5b illustrates the parts of the biomass receptacle 505 that separates the semi-refined triglycerides 526. This is a restraint screen 506 that serves as a structural envelope to the aquatic divider membrane 508. Water and triglycerides are able to pass through the aquatic divider membrane 508, while the restraint screen imposes the necessary structural ability to hold back the remaining cellulosic and other material contained in the aqueous medium 522 in which the algal biomass was cultivated.

FIG. 5c is intended to show the construction of the resistive spring mechanism 540 that is designed to work against force from the frontside or backside hydraulic press 530 or 535. The resistive spring 540 works in conjunction with the mass and volume of any algal biomass 524 contained in the biomass receptacle 505 by providing variable resistance against the hydraulic force.

FIG. 5d shows the circular extraction track 585 and illustrates the motion the harvester apparatus 500 travels to frontside or backside hydraulic press 530 and 535.

According to this embodiment of the SBES, the extraction stage 2000 shall include a circular alignment of the specialized tanks in order to correlate to the placement of Hypocycloidal Bioreactor module stacks 260 in an SBES Bioreactor Array 250. FIG. 5e shows a representation of the drain points 545 and their position beneath the SBES Bioreactor Array 250. The drain points are where the harvester apparatus 500 receives the aqueous medium 522 containing the algal biomass 524 from which triglycerides are extracted.

Figure 1:
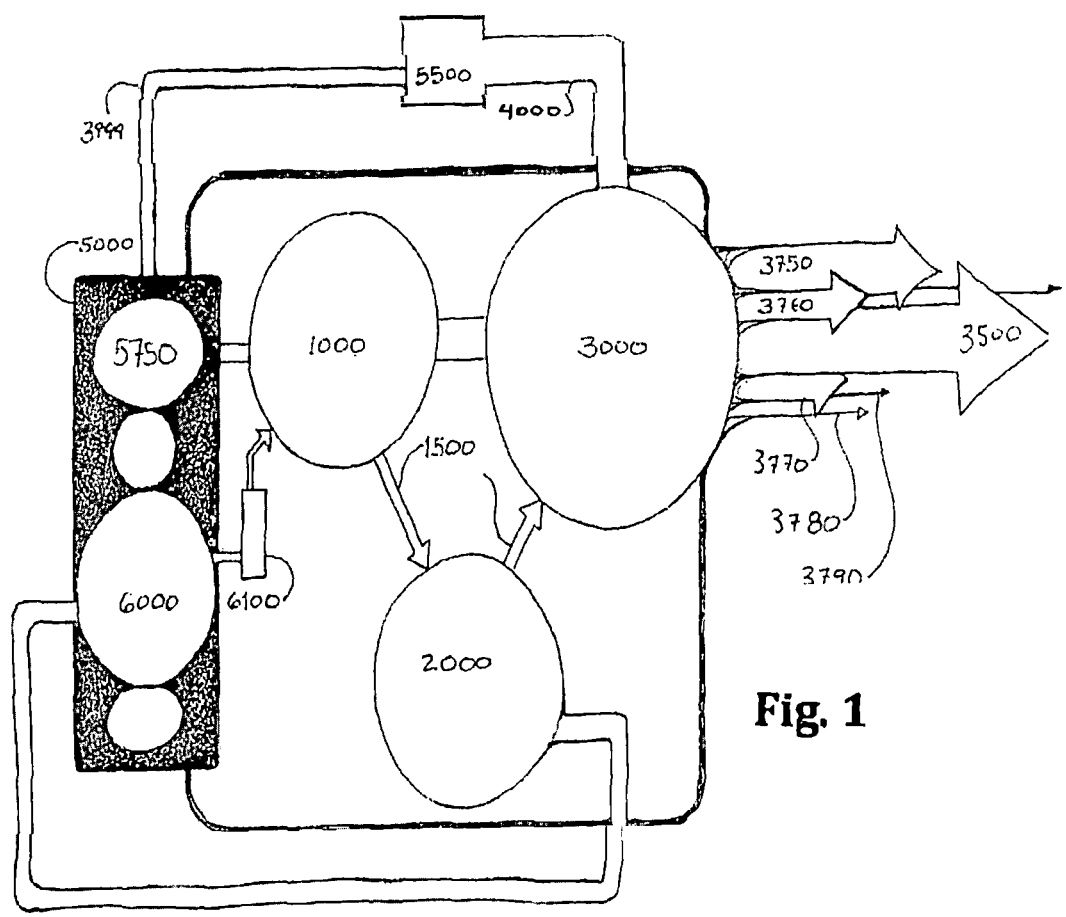
FIG. 1 is a shows a schematic overview of the SBES

As shown in FIG. 1, the semi-refined triglyceride 526 materials harvested from the extraction stage are divided into two streams. One stream is designated as SVO output to PEB Genset 2250 and sent to a specially designed tank for use in PEB Generator 6000 system. The remaining output stream from the extraction stage shall be designated as triglyceride feedstock 2750 for biodiesel production and sent to the conversion stage 3000.

This first embodiment of the extraction stage 2000, and all of its constituent system components shall be known as the Clockwork Extraction Cycle 600. However, there are variations on the specific methods of separating the triglycerides from the algal biomass, including the use of different combinations of centrifugal separators and basic chemical solvents. Despite numerous possible configurations of the Clockwork Extraction Cycle 600, the efficient production and compositional quality of triglyceride feedstock 2750 and SVO output to PEB Genset 2250 shall not vary.

The SBES Manager shall direct the two separate outputs according to networked data from instrument readings throughout various points within the entire SBES process.

Biodiesel Reaction Complex

Important elements of efficient design shall be built into the overall configuration of reactors, pumps, centrifuges, evaporators and flash vaporizers, distillation columns and other industrial apparatus in an SBES facility. All of these important elements shall be constructed in conjunction with a tank farm, which is essentially a comprehensive design that includes all of the tanks, vessels, plumbing and fixtures in connections that efficiently link all of these industrial apparatus.

A first embodiment of this comprehensive configuration is illustrated in FIG. 6a and FIG. 6b; any such comprehensive design for SBES purposes shall be known as a Biodiesel Reaction Complex. The construction of all means and mechanisms necessary for the complete and efficient conversion of algal oil triglycerides 750, 850 into refined biodiesel 3500 shall include this comprehensive configuration of important components referred to as the Biodiesel Reaction Complex. Constructing such an efficient design shall include all of the means and methods necessary for conducting the following chemical processes:

Triglyceride feedstock preprocessing
Transesterification
Alcohol and catalyst recovery
Water processing and purification
Lab facilities for fuel quality testing
Storage and dispensing The materials of construction are an especially important consideration for the Biodiesel Reaction Complex. The demands on the materials used for the storage tanks downstream of the reactor are lower since these tanks contain nearly pH neutral chemicals. The materials of construction for the Biodiesel Reaction Complex must be able to withstand basic conditions for the transesterification reaction and acidic conditions for any esterification approach used to convert free fatty acids. For the base-catalyzed transesterification reaction, stainless steel is the preferred material. However, stainless steel will not be a good choice for use in the acid-catalyzed esterification reaction because stainless steel is subject to attack by acids. Under these conditions, an acid-resistant mater such as Hastelloy should be used for the reaction vessel.

The SBES utilizes a standard transesterification process in use today by many commercial biodiesel producers. One major advantage of this process is that it is proven, predictable and basically the same at any scale. An SBES has the advantage of being less resource intensive, and is made far more efficient by using biomimetic innovation to extract every last productive ounce out of all the ingredients, and to recycle many of them for reuse. Although an SBES facility utilizes this novel and innovative approach, the basic transesterification process is still more or less the same as that used in an industrial-scale operation, or in a process located in a garage or backyard shed.

Biodiesel Reactor

The biodiesel reactor is where triglycerides are transformed into biodiesel. It is the only place in the process where chemical conversion known as transesterification occurs. Therefore, it dictates what chemical species must be handled downstream of the reactor. There are two commonly used type of biodiesel reactors used in the transesterifictaion process: batch process, and continuous process. Process flowcharts representing the two types of biodiesel reactors are shown in FIGS. 7 and 8.

The simplest method of producing biodiesel is the single reaction batch process. An updated version using two reaction tanks is used in many smaller commercial facilities usually producing less than 10 million gallons per year. The advantage of the two-tank system is that it is economical way to ensure the completeness of the reaction process and guarantees that total glycerin levels are within the ASTM D 6751 specification of less than 0.24%. An example of such a system shown in FIG. 8.

Alternatively, FIG. 7 illustrates the components of a continuous process. Continuous reactors have a steady flow of reactants into the reactor and products out of the reactor. Once a continuous flow reactor reaches steady-state operation, the product composition leaving the reactor becomes constant. The continuously-stirred-tank-reactor (CSTR) process is an improvement on the batch system because, as the name implies, feedstock oil and reactants are continuously added to the process without the need to charge and discharge large, fixed-volume tanks. This greatly increases the process efficiency, and for this reason is an aspect of the first embodiment. The CSTR replaces the batch tanks with a series of long, tubular structures containing internal obstructions that cause the reactants to mix as they are pumped through the unit. Varying the speed of transit through the CSTR will vary the time the reactants are in contact with each other, improving the reaction completeness.

Biodiesel Technologies GmbH is an Austrian manufacturer of high-capacity small-size CSTR units. Their CPU-1000 unit is delivered ready to operate after connecting it to external sup and storage tanks for feedstock oil, ethanol, water, steam, compressed air and electrical power. The innovative design of the CPU-1000 unit makes it an ideal component in the construction and configuration of the preferred embodiment of an SBES facility.

There are also many other manufacturers that currently offer complete systems and other advanced biodiesel equipment. One example of such equipment is the BioPro380, a self-contained automated biodiesel processor available from Springboard Biodiesel, LLC 341 Huss Drive Chico, Calif. 95928. Standardized, affordable, and readily available pumps, motors, tanks, tools and other industrial equipment can also be shipped directly from commercial suppliers.

The Biodiesel Reaction Complex shall be capable of efficient automation of all necessary monitoring and regulation through the construction of control loop mechanisms utilized by the SBES Manager.

Pumps

While the role of pumps in a chemical plant may seem mundane, they are actually a critical part of the SBES. A properly designed and utilized system of pumps is what will allow chemicals to be moved through the system in an efficient way. The most common type of pump in the chemical industry is a centrifugal pump. In many applications, the fluid shear introduced by a centrifugal pump is not a point of concern. However, the shear created by a centrifugal pump can create problems for product streams within the SBES. The amount of fluid shear imparted by the pump can be significantly reduced by using a positive displacement pump. There are a number of different types of positive displacement pumps including gear pumps (external and internal) and lobe pumps.

While leaking pumps seals or impeller wear can be operational issues with pumps, the most common issue with pumps is the loss of suction pressure. Suction pressure is the pressure supplied to the suction side of the pump by the liquid. During loss of suction pressure, which is known as cavitation, the pump discharge pressure and discharge flow rates become erratic and low. Cavitation is created by vaporization of liquid at the pump suction. This situation can be created by a plug in the suction piping or by starting the pump up too rapidly. In general, positive displacement pumps are more difficult to cavitate than centrifugal pumps.

The most significant aspect of constructing SBES pump systems will involve the complete removal of potential electrical hazards through the use of pneumatic motors. Within any SBES facility, all motors within pumps shall be driven pneumatically with compressed air. Safe, reliable and commonly available types compressed air systems can easily be adapted to provide power for industrial motors used throughout an SBES facility. Finally, to add further efficiency to pneumatic pump systems, they are monitored and automated by the SBES Manager.

Centrifuges

An important aspect of the first embodiment of the transesterification process involves accelerating the chemical separation with the use of a device in which the materials of different densities are separated by rotating them in a horizontal circle. As this device spins, it creates an artificial, high-gravity field that causes the denser particles of matter to move to a greater radius of rotation, while displacing the lighter particles. This type of device, known as a centrifuge, is commonly available from industrial equipment suppliers and shall be used to separate the materials flowing through various stages of the Biodiesel Reaction Complex. Centrifuges as part of the construction of Biodiesel Reaction Complex must ensure that chemical separation can be completed rapidly and effectively. Different centrifuge configurations are available, many of which being very amenable to continuous operation. The only real disadvantage of the centrifuge is its initial cost, and the need for considerable and careful maintenance. However, centrifuges are used extensively in the food processing, rendering, as well as biodiesel industries.

The performance of a centrifuge depends on its specifications as well as the characteristics of the mixture to be separated. While centrifuges are generally rated in terms of mixture-handling capacity, the product quality specifications are the most important consideration. The choice of appropriate centrifuge type and size are predicated on the degree of separation needed in a specific system. The viscosity of the liquid has important implications on the choice of centrifuge size since higher viscosity fluids are more difficult to handle.

Ultimately, all means and mechanisms associated with centrifugal separation shall be linked to the SBES Manager control loop.

Evaporators and Flash Vaporizers

Another means of separating chemicals in a fluid mixture is by exploiting the differences in boiling points between the chemicals. If the boiling points are sufficiently different for the chemicals to be separated, such as with water and biodiesel, an evaporator or flash vaporizer can be used for the separation. In the evaporator, the liquid is heated to a temperature in which only the more volatile chemical species will vaporize. As such, the vapor stream leaving the evaporator will be enriched in the more volatile species and the liquid stream from the evaporator will be enriched in the less volatile species. In an evaporator, the separation is accomplished by supplying heat while the mixture is held at a fixed pressure. In contrast, a flash vaporizer first heats the liquid at an elevated pressure. Then, the heated liquid is sent through a flash valve that decreases the pressure. The decrease in pressure causes the more volatile portion of the liquid mixture to vaporize.

As with all other aspects of Biodiesel Reaction Complex instrumentation, all means and mechanisms associated with chemical mixture separation shall be linked to the SBES Manager control loop.

Distillation Columns

An important separation device for miscible fluids with similar boiling points (e.g., ethanol and water) is the distillation column. Separation in a distillation column is predicated on the difference in volatilities between chemicals in a liquid mixture. In a distillation column the concentrations of the more volatile chemical species are enriched above the feed point and the less volatile species are enriched below the feed point. The vaporization in the column is driven by heat supplied in the reboiler, which is subsequently removed in the overhead condenser. The temperature in the distillation column is the highest at the bottom and decreases moving up the column. Distillation column can either use trays or packing.

The degree of separation that can be achieved in a distillation column is dictated by the relative volatilities of the chemicals to be separated, the number of trays, or the height of the packing and the reflux ratio. Chemicals with very different boiling points are easier to separate than those with similar boiling points. Increasing the number of trays or the height of packing can increase the amount of separation. Reflux ratio is the amount of condensed overhead vapor that is fed back in the top of the column. Increasing the reflux ratio increases the degree of separation. Increasing the number of trays or height of packing increases the column height, and increasing the reflux ratio increases the column diameter. Either of these increases in column dimensions increases the capital cost of the column.

Trayed distillation columns are the most common. A tray is where contact occurs between the vapor stream and the liquid stream. The liquid enters the feed tray through the downcomer from the above tray, flows across the tray where it interacts with the vapor, spills over a weir, and finally flows through the downcomer to the next tray. The vapor flows up through the holes in the tray. It is important to have appropriate flow rates of the liquid and vapor to get optimal column operation. If the liquid flow rates become too high, poor contacting occurs with the vapor and extreme flooding of the column can occur. The onset of flooding in a column is easy to observe since the column's pressure drop will increase markedly when flooding begins. If the vapor flow rate is too high, liquid can be entrained and carried over to the above tray leading to poorer separation. In contrast, too low of a vapor rate can lead to weeping of the liquid through the tray, which diminishes the separation. The liquid and vapor flow rates are dictated by the operation of the reboiler and the condenser, which means they are controlled by the energy input and removal. All of the means and mechanisms associated with distillation columns shall be directly linked to the SBES Manager control loop.

Tank Farm

Building an SBES facility shall include the construction of a specialized configuration of containers and tanks capable of handling all raw materials, finished products and value-added byproducts. This also includes all necessary plumbing and fixtures in order for the efficient movement of materials throughout this specialized configuration of tanks and containers. This configuration of containers shall be known as an SBES tank farm, and shall be designed to function in an integrated way within its geographical ecosystem in full accordance with biomimetic concepts. A first embodiment of this aspect of the Biodiesel Reaction Complex is shown in FIGS. 6, 6a, 6b.

Ultimately, all of these major parts shall be constructed according to the biomimetic concepts that integrate the entire SBES facility as a unit within its ecosystem. The end result is an efficiently functioning system that is both ecologically sustainable and economically profitable.

DETAILED DESCRIPTION

Operation Section

To begin a description outlining the operation of an SBES facility, it is necessary to outline its three stages:

Cultivation Stage
Extraction Stage
Conversion Stage
SBES Manager (SBES operation requires an SBES Manager to regulate SBES industrial metabolism.)

And as the following description goes further, each of the steps in the operation of the SBES facility are described in detail with drawing figures and reference numerals in parenthesis where applicable.

In the Cultivation Stage 1000, the operation includes everything necessary in order to cultivate algae. Operational steps in the Cultivation Stage shall begin with a careful selection of algae species.

Algae Selection

Since the purpose of an SBES is primarily to produce biofuel and electricity from the raw material of algal biomass, algae selection is important. Biological information regarding algal species must be taken into consideration. The selection of algal species must be directly related to location, configuration and construction of an SBES facility. In selecting an appropriate species of algae for SBES operation, safety and security mechanisms shall be built into the operational procedures of any SBES facility. These will, of course, include all applicable laws and regulations that are standard in the operation of any industrial facility, but must also include an overall respect for the balance of any ecosystem.

Decisions regarding species selection and related aspects of SBES operation should include careful considerations regarding the local ecosystem in which an SBES is installed and operated.

Specially selected or genetically modified strains of algae are grown in Hypocycloidal Bioreactors and fed waste carbon dioxide from the exhaust of the PEB generator system. Whether specially selected, or genetically modified, or any combination thereof, it is of the highest priority to make careful considerations regarding the environmental impact potential of algae, and the possibility of Hypocyloidal Bioreactor Modules releasing invasive species into ecosystems.

It is important to look at the full environmental impact of an SBES facility. These considerations shall include careful selection of native species for use in their originating ecosystems and safety mechanisms built into the genetic structures and also into the construction and operation of Hypocyloidal Bioreactor Modules.

Operating the cultivation stage involves means and methods of filling Hypocycloidal Bioreactor Modules 200, Operation of Photothermal Generators 300, Operation of Hydrocycle Subsystem 5500, and operation of the SBES Manager 5000 in order to monitor conditions, implement control and regulate SBES industrial metabolism. Finally, once algal biomass is ready for harvest, the final step in the cultivation stage involves draining the Hypocycloidal Bioreactor Modules. Gravity exerts force upon the materials within the Hypocycloidal Bioreactor Modules, so that the output of the Cultivation Stage simply drains into the Extraction Stage.

In the Extraction Stage 2000, the operation includes everything necessary in order to extract triglycerol feedstock, and properly separate streams of other materials from the cultivated algae. This consists of a series of operational steps including:

Receiving the algal biomass output 1500 from the Cultivation Stage 1000, operation of all of the means and mechanisms that comprise the Clockwork Extraction Cycle 600, frontside hydraulic press 530 and backside hydraulic press 535, the regulatory activities of the SBES Manager that include monitoring and precise control of all operations which ultimately separate the high-quality oil from the algal biomass. The SBES manager divides the oil output of the Extraction Stage into SVO output to PEB Genset 2250, and Triglycerol feedstock 2750 output to Conversion Stage.

There can be wide variations on the specific methods used to separate triglycerides from algae. However, a first embodiment of the extraction stage consists of a Clockwork Extraction Cycle 600. The Clockwork Extraction Cycle functions according to a timetable based on the rate of algae growth within each of the Hypocycloidal Bioreactor Modules combined with the rate of other mechanisms involved with the Extraction Stage processes.

At the base of every Hypocycloidal Bioreactor Module, its contents drain into a specially designed tank. This specially designed tank operates according to precise timing that moves it along a circular track, or tank track 585 to the frontside hydraulic press 530 and backside hydraulic press 535, as shown in FIG. 5d.

This circular alignment of drain points shall be determined by dividing the circumference by 14. This division allows for the proper placement of 6 drain points and 2 hydraulic presses along the tank track, as shown in FIG. 5e.

Every 4 hours the harvester assembly moves along the tank track to receive algae ready for harvest. The harvester assembly moves according to clockwork rotation to its corresponding hydraulic press.

The pattern of this process is automated by timing controls set to a precise timetable that correlates stops in positions at drain points. The SBES Manager administers this automation. Each day of operation is divided into 6 periods; however, time segments can vary with differing rates of cultivation, facility parameters, or other conditions.

This process of monitoring, analysis and control involves allocating specific periods for draining, separation, and extraction according to a precise timetable correlated to stops in positions at drain points along the tank track. A Clockwork Timetable administered by the SBES Manager dictates the specific periods, and is shown below in Table 1.

TABLE 1

| Clockwork Timetable | | | |
| --- | --- | --- | --- |
| 2000 hrs | FS Drainpoint 1 | 2400 hrs | BS Drainpoint 1 |
| 1600 hrs | FS Drainpoint 2 | 400 hrs | BS Drainpoint 2 |
| 1200 hrs | FS Drainpoint 3 | 800 hrs | BS Drainpoint 3 |
| 800 hrs | FS Drainpoint 4 | 1200 hrs | BS Drainpoint 4 |
| 400 hrs | FS Drainpoint 5 | 1600 hrs | BS Drainpoint 5 |
| 2400 hrs | FS Drainpoint 6 | 2000 hrs | BS Drainpoint 6 |

FS Drainpoints are designated with an FS prefix to indicate that they correspond to the Frontside Hydraulic Press 530; BS prefixes indicate correspondence to the Backside Hydraulic Press 535. As shown in the above table, each day of operation is divided into 6 periods. However, time segments can vary with differing rates of cultivation, facility parameters, or other conditions.

Next, the Clockwork Extraction Cycle moves the collected biomass to a hydraulic press along a tank track. As the hydraulic press exerts force upon the biomass contents in the receptacle, triglycerides and other associated components of the algae are pressed through the membrane and extraction screen, while cellulosic matter and other organic material remain in the receptacle.

The pressure exerted upon the algal biomass by the hydraulic press is ultimately controlled by a resistive spring mechanism. The resistive spring works in conjunction with the mass and volume of the algal biomass contained m the receptacle, by providing variable resistance against the hydraulic force.

The harvester module is where the algal biomass is then separated from the water, and triglycerides are extracted. The steam and triglycerides are then fed into a transesterification process that converts the algal oil into biodiesel.

This aspect of the extraction stage accomplishes a significant step in the refinement of the algal triglycerides. The operation of extraction mechanism efficiently separates triglycerol content from algal biomass using hydraulic force. Another step, often necessary in many embodiments of SBES technology, shall further refine said triglycerol content through a combination of industrial centrifuges and solvents. Of course, such methods are easily accomplished through the use of standard industrial apparatus, and are well known by those skilled in the art and trade of the biofuel industry.

The final step in the extraction stage consists of an efficient means of dividing the final output stream of the refined algal oil into two distinct feedstock sources. One stream of output is sent as SVO output to PEB Genset 2250, and the other stream is sent as triglycerol feedstock 2750 output to Conversion Stage.

The pattern of this entire process is regulated by a specialized control loop and administered by the SBES Manager.

In the Conversion Stage 3000, the operation includes everything necessary in order to process all triglyceride feedstock through all of the components of the Biodiesel Reaction Complex. The conversion stage converts the triglycerol feedstock produced from the extraction stage into biodiesel and consists of a series of operational steps including:

Triglycerol feedstock preprocessing, transesterification, alcohol and catalyst recovery, glycerol refining, water processing and purification, laboratory facilities for fuel quality testing and refinement (ensuring ASTM D 6751 standardized final biodiesel output), storage and dispensing, and all other related considerations. Throughout the process, operational steps shall be in compliance with all applicable regulatory and safety standards. This series of operational steps is conducted in the Biodiesel Reaction Complex, and ultimately monitored and controlled by the SBES manager, ensuring ASTM D 6751 standardized final biodiesel output.

What will be necessary for transforming algae oil into diesel fuel is a process known as transesterification, or the transformation of one form of ester into another. Esters are naturally occurring compounds formed when an acid and alcohol are mixed. Esters can be found in the oil within the algae. Algae oil, as well as any other type of vegetable oil, can be technically described as a triglyceride, or three fatty acid chains and glycerin combined into one oil molecule. Transesterification involves breaking the chemical bonds within the oil, separating every oil molecule into three fatty acid chains and a free glycerin molecule.

During the process, alcohol is added, and each of the fatty acid chains attaches to one of the new alcohol molecules, creating three mono-alkyl esters. This decreases the viscosity of the esters and results in a fuel suitable for use directly in compression-ignition engines. Once completely separated from the glycerin, the alkyl ester chains are what are known commercially as biodiesel.

The alcohol used in the process can be ethanol or methanol. Methanol is the current standard within the industry, however it has some disadvantages. Methanol distilleries commonly generate substantial carbon emissions. Methanol is also highly corrosive, dissolves rubber, can be fatal if ingested, and must be handled with extreme caution. Ethanol, on the other hand, can be a much more environmentally friendly resource, but is generally more expensive and may not always provide a stable and consistent reaction.

These challenges can be overcome by the intelligent use of cellulosic ethanol. Cellulosic feedstock contains lignin. Lignin binds the cellulose molecules together and can be extremely difficult and expensive to break down. To unlock the cellulose molecules from the lignin, the feedstock is often pre-treated with heat and acids. The pre-treated cellulose is then mixed with specialized enzymes to break down the cellulose into sugars. One embodiment of this pre-treatment process may include engineered enzymes. The specially engineered enzymes shall be modeled after biologically efficient substance found in the guts of termites: Acetogen.

Therefore, it is easy to include cellulosic material as a value-added byproduct in the SBES process, through the use of proprietary substances made with genetically modified microbes and enzymes. These specialized enzymes are widely available, and being developed in the United States biotech industry. Once the cellulosic materials have been broken down, the resulting dark brown goo, with a slightly sweet, molasses-like aroma is fed into fermentation tanks where bacteria or yeast go to work to produce ethanol.

Triglycerides combined with ethanol yield biodiesel. Thus, transforming algae into diesel fuel is a relatively straightforward process. However, there is still one more crucial element needed as a catalyst in order to make the transesterification work. To initiate a reaction between the triglycerides and the ethanol, sodium hydroxide is the preferred catalyst. Sodium hydroxide is commonly referred to as caustic soda, and is the same chemical used to unclog household kitchen drains. The specific quantity of sodium hydroxide needed depends on the acidity, or pH, of the oil. Once careful measurements are made, the sodium hydroxide is mixed with the ethanol. The resulting solution is then added to the triglycerides, and agitated by stirring and heating for a specific length of time. The catalyst solution "cracks" the triglyceride molecules and releases the alkyl esters, or raw biodiesel, and the separation process begins. The freshly formed biodiesel rises to the top of a settling tank, while the glycerin and catalyst settle to the bottom. This type of transesterification is currently in common use and is widely known by and used by anyone skilled in the art.

The two-tank batch process is often the simplest, most straightforward means of producing marketable quantities of biodiesel. However, a first embodiment of the SBES makes one substantial modification to the two-tank batch process. The SBES simply updates this conventional batch-process by changing it into a continuous process. This is accomplished by replacing each of the two batch tanks with continuously-stirred-tank-reactors. A continuously-stirred-tank-reactor (CSTR) has a steady flow of raw materials into, and finished products out of, the unit. Once a continuous flow reactor reaches steady-state operation, the product composition leaving the reactor becomes constant. With the additional mechanisms necessary for the operation of dedicated input pumps, centrifuges, instrumentation and control, the CSTR units can easily be used in place of the batch tanks. FIGS. 7 and 8 illustrate this process modification.

The continuously-stirred-tank-reactor (CSTR) process is an improvement on the batch system because, as the name implies, feedstock oil and reactants are continuously added to the unit without the need to charge and discharge large, fixed-volume tanks. This greatly increases process scalability and efficiency, and for this reason is an aspect of the first embodiment. The CSTR replaces the batch tanks with a series of long, tubular structures containing internal obstructions that cause the reactants to mix as they are pumped through the unit. Varying the speed of transit through the CSTR will vary the time the reactants are in contact with each other, improving the reaction completeness.

Transesterification operations within the Biodiesel Reaction Complex are very common chemical processes. The general methods of operation for an SBES facility regarding triglyceride feedstock as it is processed in the conversion stage, through all of the components of the Biodiesel Reaction Complex is very standardized and straightforward. In fact, except for the novel aspects of the SBES Manager, its control over the SBES industrial metabolism, and the overall design adherence to biomimetic principles, the Biodiesel Reaction Complex utilizes a tried and tested form of transesterification.

Reference numerals 750 through 831 illustrate the standard transesterification process in common use within the current biodiesel industry. As can be seen by the illustrations of FIGS. 7 and 8, the two transesterification processes are nearly identical. The only substantial difference is in the replacement of batch tanks with CSTR units, in order to facilitate continuous operation. This substantial difference can be shown by comparing FIGS. 7 and 8, and noting that the following components in the batch process: batch tank input pump 1 810, batch tank input pump 2 812, batch tank 1 814, batch tank 2 816, mixer 817; have been replaced by the following components in the continuous process: CSTR main input pump 1 710, CSTR main input pump 2 712, CSTR 1 714, CSTR 2 716, Centrifuge 717.

Thus, a first embodiment of an SBES is operated with this improvement upon the conventional batch process created by simply replacing batch tanks with CSTRs. This allows an SBES facility to accomplish the conversion of much larger volumes of triglycerides on a continuous basis. This important design aspect of the Biodiesel Reaction Complex allows an SBES facility to be much more profitable using less overall process energy to ultimately produce a greater output. Operation in a continuous mode also allows greater control over process variables and specific separation and purification steps. The pattern of these steps shall be regulated by a specialized control loop and administered by the SBES Manager.

SBES Manager

The SBES Manager utilizes common industrial control means and methods that are available and practical to anyone knowledgeable of current conventions within the biofuel and energy production sectors. However, there are some additional features in the conceptual framework, construction, and industrial metabolism that allow the operation of the SBES Manager to possess unique advantages and capacities.

The capacity to dynamically control the SBES production process, and simultaneously integrate it within its economic and ecological environments creates revolutionary advantage. This unprecedented level of control and integration is made possible through the operation of the SBES Manager. In describing the operation of the SBES Manager, it is necessary to explain the SBES Manager Control Loop. To fully describe the SBES Manager Control Loop is to fully describe the activities of specific components of the SBES that produce accurate measurements, analytical processes, and the resulting signals that trigger automated control mechanisms, such as pneumatic motors 920 and automated valves 922.

In the Cultivation Stage, an important control variable is the properties of the algae feedstock used as input into the biofuel processing stage. It is therefore a key element is in the instrumentation and control loop.

In the Extraction Stage, efficient extraction and separation of the biomass is what allows a SBES facility to operate efficiently. Therefore SBES Manager operation of the control loop shall include means and methods of control over the timing and operation of Clockwork Extraction.

In the Conversion Stage, process variables include temperature, pressure, level, and flow rate. Therefore, instrumentation and control shall be operated on these variables throughout the Biodiesel Reaction Complex. Important issues of both accuracy and precision have been addressed in the design of the Biodiesel Reaction Complex.

The following instrumentation shall be used in the Conversion Stage control loop:
Pressure Transducers
Level measurement
Flowmeters
Thermocouples Pressure Transducers The most common pressure measurement instruments used in SBES Manager control loop are electrical sensing devices, which are known as strain gauges. Strain gauges are predicated on the fact that the electrical resistance of conducting solids changes with length and diameter of the solid. The dimensional change of the solid induced by a pressure causes an increase in the electrical resistance of the conducting solid. This conducting solid is known as a diaphragm 926. An elastic element 925 or electrical sensing device used to measure pressure is called a pressure transducer 924. The pressure tap 927 for a transducer 924 should be located in the vapor phase a process. A transducer located in the liquid phase will detect a different pressure at different depths in the liquid.

To use a pressure transducer 924 for process control or in continuous monitoring, the transducer must produce an electrical signal. For the elastic element device, the direct pressure reading due to displacement must somehow be converted to an electrical signal. An advantage of the electrical sensing approach is that these devices directly provide an electrical signal.

As with thermocouples, pressure transducers shall be utilized by the SBES Manager control loop by comparing the measured pressure to a desired set point pressure.

Level Measurements

Level measurement can be used to yield mass balance information throughout the SBES. Historically, level measurement devices have typically been displacer-based meters or differential pressure meters. The displacer-based meter 934 is based on buoyancy. The displacer is immersed in a displacer chamber 936 that is located as a side chamber. The displacer is restrained by an elastic element whose motion is proportional to the buoyant force, so the level can be determined by the vertical location of the displacer. Differential pressure meters 944, which are the most common level indicating devices, measure the difference in pressure between two pressure taps in a vessel. It is important to note that both of these level measurement indicators are liquid density dependent, so that changes in liquid densities can affect their readings. This effect can be particularly important if several liquid phases are present in the device. For example, the height of liquid in a gauge glass connected to a vessel is not a direct measurement of the liquid level. Recently, level measurement devices have been developed that use signal reflectance from an ultrasonic transducer or radio frequency, which measures the change in impedance between two capacitor electrodes.

In addition to density, there are a number of factors that can influence the reliability of a level measurement. Plugged taps can occur without causing apparent discrepancies in the level measurement device. Excursions to high liquid levels can impact the reliability of the level measurement as can the presence of foam in the vessel.

The measurement and control of level in a vessel generally requires two taps into the vessel. It is important that these taps are properly valved. Since the level indicator can be used to monitor the amount of material in a vessel, it can be used to track chemical inventory within a process as well as to control the charging of chemicals into a batch process. Level measurements can be converted to electrical signals that can be used for control, easily allowing these instruments to be used in the SBES Manager control loop in ways that monitor and control flow rate through the operation of automated pumps.

Flowmeters

The final process variable that will be discussed is flow rate. Flow rate measurement will generally only be needed if a continuous flow process is used. There are a number of methods for measuring flow rates, but the most commonly used approaches in chemical processes are different pressure flowmeters and positive displacement flowmeters. Differential flowmeters measure the difference in pressure between the two sides of a restriction in a confined stream. These instruments are based on restrictions imposed by a venture tube, an orifice plate or a flow nozzle with the orifice plate meter being the most common. The orifice plate hole should be appropriately sized for the flow rate range of interest. If the hole is too large the resulting pressure change and, therefore, accuracy of the flow measurement will be inaccurate. In contrast, if the hole is too small, the flow rate measurement is at the cost of too high of a pressure drop. While orifice plate meters are typically used for flow rate measurement and subsequent control, it should be noted that the meters do have some potential problems. First, this type of flowmeter is highly dependent on the density and viscosity of the liquid. Orifice plates can erode or have blockage, which will lead to inaccurate measurements. The pressure taps can become plugged leading to erroneous flow values.

Positive displacement flowmeters measure flow rates using the fluid to displace a measuring device. Most common are rotary displacement flowmeters. In these meters, flow rate is measured by the amount of rotation created by the flow of fluid past a rotary device. An example of a rotary flowmeter is a vane-liquid flowmeter in which a set of vanes mounted on a rotor with opposing pairs rotated in a cylindrical chamber.

These instruments shall be used in the SBES Manager control loop in ways that monitor and control flow rate through the operation of automated pumps.

Thermocouples

The most common process variable monitored in the SBES is temperature. The temperature at a specific point is generally measured using thermocouples 950, which are electric devices. Thermocouples 950 are made of two different metallic wires 958. These wires are connected at a junction 952 and an electrical current is established when the junction is heated. The electrical current is proportional to temperature at the junction. For this reason, the thermocouple 950 must be calibrated to correlate temperature to current. Thermocouples are categorized by the metals use in their junctions, with different metal junction combinations being more appropriate for different temperature ranges. The supplier does typically not calibrate individual thermocouples. Instead, manufacturers will typically test a representative portion of the thermocouples that they produce. Due to the manufacturing procedure, thermocouples can be inaccurate, so individual testing and collaboration should take place before beginning operations. The thermocouple is typically enclosed within a thermowell 954. The thermocouple must be fully inserted into the thermowell 954 with the thermowell 954 extended appropriately into the vessel wall 955 and protected by an external cap 956. This extends the thermocouple in the process to obtain a correct reading. If the temperature of a process liquid is being measured it generally adequate for the thermowell 954 to extend 2-3 inches into the liquid. Due to inferior heat transfer, the thermowell should extend about six inches into a process vapor.

Thermocouples are typically used in processes for both monitoring and controlling the process. When a thermocouple is used as part of a process control loop, the electrical current output from the thermocouple is compared with the current expected for the set point temperature. Deviation of the actual temperature from the set point temperature will trigger a heater or cooler included in the SBES Manager control loop.

In addition to these issues, there are a number of other factors that are important to the operation of the SBES Manager control loop. In addition to the general importance of cost, precision, and reliability as key roles in the operation of the control loop of the SBES Manager, there is one specific factor that is very important. This important factor is the operator interface.

The SBES Manager shall be equipped with an operator interface that will give the operator real-time information about how much power they are using at any given time. Users see a clear digital readout of how much energy is being consumed, as well as its cost. With this information at the user's fingertips, the user can adapt to dynamic economic, social, and physical parameters.

With specially engineered power distribution capabilities with variable energy inputs and outputs, The SBES Manager is able to store and release energy based on various factors, including cost and demand which increases efficiency by avoiding the power peaks that can tax the power grid. For example, biodiesel and electrical output can be adapted to meet volatile fluctuations in market demand. When electrical output demands are decreased, biodiesel output is increased. When biodiesel output is decreased, electrical output is proportionately increased. This electrical output can be dynamically linked with an electric utility using compatible transmission equipment that is UL listed and installed per the state electrical code. Or this dynamic link can be easily switched to accommodate consumption by industrial manufacturing.

The user interface of the SBES Manager enables many different kinds of users with a wide of range of individual skillsets to directly interact with the SBES process. This translates not only to the "how," but also the "why" of any SBES facility operation. Users are at full liberty to implement other intelligent applications of the SBES process.

In addition the growing demand for biodiesel, the electricity output of an SBES facility has revolutionary potential. SBES electrical output can directly accommodate the energy needs of hydrogen and fuel cell production systems, kinetic energy storage in flywheel systems, seawater desalination systems, as well as residential and commercial heating and air conditioning systems. Any SBES can be operated in various embodiments and at various scales, working as decentralized power generation. Linking many decentralized SBES power sources into regional "smart-grid" networks will make our communities and our power sources cleaner, safer, and steadier.

The SBES Manager efficiently handles all the transfers of materials, mechanisms and information throughout the SBES. The SBES Manager shall be equipped with an intuitive used interface that enables lab technicians, facility staff, and end users to customize and control their interaction with the SBES, based on access to detailed information regarding SBES industrial metabolism. This finally comes down to enabling the SBES to be linked and integrated with ecology, individuals, and entire communities.

Ultimately, all these stages of operation shall be designed to function according to biomimetic concepts that effectively span the metabolic rift between society and nature. The end result is an efficiently functioning SBES facility with a sustainable biodiesel output that shall meet or exceed specifications defined by the ASTM D 6751 standard; and a sustainable electrical output compatible with "smart grid" transmission equipment that is UL listed and installed per the state electrical code.

CONCLUSION, RAMIFICATIONS, AND SCOPE

Accordingly, the reader will see that the System of Biomimetic Energy Synthesis (SBES) in the described embodiments can be used to overcome some of the many challenges to developing new sources of clean, sustainable energy derived from a biological source. From the description above, a number of advantages of some embodiments of the SBES become evident:

Broad public support for environmentally friendly technology allows it to be implemented into local communities and marketed effectively;

Due to its innovative design and modular construction, energy facilities can be built to scale and easily replicated;

Competitively priced, reliable streams of electrical energy and biofuel can be made available to industrial consumers;

The creation of meaningful, high-paying jobs;

Multiple energy products and value-added byproducts are produced;

Substantial reduction in carbon emissions, as well as lowered levels of hydrofluorocarbons, perfluorocarbons, and sulfur hexafluoride, and other harmful gases from being released into the atmosphere;

Mitigation of negative health effects within communities;

Less damage to wildlife due to less demand for petroleum exploration and development;

Fulfillment of local communities stated desire for aesthetic beauty and economic security.

While the above description contains much specificity, this should not be construed as limitations on the scope, but rather as an exemplification of one preferred embodiment thereof. Accordingly, the scope should be determined not by the embodiments illustrated and described, but by the appended claims and their legal equivalents.

For example, many other variations are possible. The SBES can be implemented aboard oceangoing vessels for mobile and international energy production. As mentioned earlier in this document, additional embodiments of the system can also be configured to meet the power demands of hydrogen production, flywheel and other forms kinetic energy storage, and seawater desalination projects. These embodiments make innovative use of the electrical output of the SBES. Other uses for the SBES electrical output also include energy production applications for the industrial sector.

The SBES will be useful in producing renewable energy for many types of facilities and equipment used for producing, processing or assembling goods. The SBES output can be used as energy input to a wide variety of manufactured products. Energy use in many of these sectors is largely for process heat and cooling and powering machinery, with lesser amounts used for facility heating, air conditioning and lighting. The SBES has the additional advantage of producing high-quality biodiesel as well as electricity. Thus, energy intensive activities that can be supported through the production of electricity as well as biodiesel in industrial engines include the following sectors:

| | |
|---|---|
| Manufacturing | (NAICS codes 31, 10) |
| agriculture, forestry, fishing and hunting | (NAICS code 11) |
| mining | (NAICS code 21) |
| construction | (NAICS code 23) |

The invention has been described in connection with certain preferred embodiments; however, it will be appreciated that it is susceptible to various modifications, changes and adaptations, all of which are intended to be comprehended within the meaning and range of equivalents of the appended claims.

What is claimed is:

1. A system for cultivating photosynthetic algal biomass comprising:
   at least one bioreactor module comprising:
   vertically arranged four cylindrical tanks with a hypocycloidal space in a center thereof, each of the four cylindrical tanks comprises an interior surface that is light-reflective, and wherein the four cylindrical tanks configured to grow algal biomass;
   a photothermal generator arranged within the hypocycloidal space, and
   wherein the photothermal generator is configured to irradiate light to the algal biomass inside the four cylindrical tanks,
   a harvester apparatus comprising:
   a biomass receptacle comprising a screen enclosing a membrane, the biomass receptacle configured to receive the algal biomass from the at least one bioreactor module;
   a drain compartment in fluid communication with the biomass receptacle and configured to receive content from the biomass receptacle;
   a process tank having a drain aperture in communication with the drain compartment; and
   an extraction canister housing the biomass receptacle, drain compartment and the process tank;
   a conversion apparatus comprising:
   two reactors in communication with the harvester apparatus, the two reactors configured to receive content from the harvester apparatus; and
   a pump coupled to each of the two reactors; and a heat exchanger comprising:
at least one housing including an evaporator housing formed of thermally conductive material, wherein the evaporator housing containing a refrigerant, and wherein the evaporator housing is thermally coupled to the photothermal generator and configured to remove heat generated by the photothermal generator.

2. The system of claim 1, wherein the photothermal generator is a high-intensity discharge lamp.

3. The system of claim 1, wherein the at least one bioreactor module includes a plurality of bioreactor modules.

4. The system of claim 3, wherein the plurality of bioreactor modules is interconnected with one another to form a vertically stacked hypocycloidal bioreactor modules.

5. The system of claim 4, wherein the vertically stacked hypocycloidal bioreactor modules having a base fitted with a drain and a top section coupled to a cap.

6. The system of claim 1, wherein a portion of each of the four cylindrical tanks are formed of a transparent material.

7. The system of claim 1, wherein an exterior surface of the evaporator housing is light-reflective.

8. The system of claim 1, wherein the harvesterapparatus is configured to be disposed on a traction track.

9. The system of claim 1, wherein the biomass receptacle further comprises a spring.

10. The system of claim 1, wherein the extraction canister comprises a drain output having a drain valve.

11. The system of claim 1, further comprises a generator set coupled to the extraction apparatus.

12. The system of claim 1, wherein the system further comprises a hydroelectric generator coupled to cooling tanks through a pipe.

13. The system of claim 12, wherein the cooling tanks are coupled to a steam pipe in communication to the extraction apparatus.

* * * * *